US012714693B2

(12) United States Patent
Lewin

(10) Patent No.: US 12,714,693 B2
(45) **Date of Patent: *Aug. 25, 2026**

(54) USE OF SPLA2 INHIBITORS TO TREAT ENVENOMATION BY SNAKES AND WASPS

(71) Applicant: Ophirex, Inc., Corte Madera, CA (US)

(72) Inventor: Matthew R. Lewin, Corte Madera, CA (US)

(73) Assignee: Ophirex, Inc., Corte Madera, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/000,226

(22) Filed: Dec. 23, 2024

(65) Prior Publication Data

US 2025/0120949 A1 Apr. 17, 2025

Related U.S. Application Data

(63) Continuation of application No. 16/097,160, filed as application No. PCT/US2017/030436 on May 1, 2017, now Pat. No. 12,383,531.

(60) Provisional application No. 62/423,693, filed on Nov. 17, 2016, provisional application No. 62/340,075, filed on May 23, 2016, provisional application No. 62/329,611, filed on Apr. 29, 2016.

(51) Int. Cl.

| | |
|---|---|
| ***A61K 31/4045*** | (2006.01) |
| ***A61K 31/192*** | (2006.01) |
| ***A61K 45/06*** | (2006.01) |
| ***A61P 39/02*** | (2006.01) |

(52) U.S. Cl.

CPC .......... *A61K 31/4045* (2013.01); *A61K 45/06* (2013.01); *A61P 39/02* (2018.01)

(58) Field of Classification Search

None

See application file for complete search history.

(56) References Cited

U.S. PATENT DOCUMENTS

| | | | |
|---|---|---|---|
| 5,064,817 | A | 11/1991 | Yedgar et al. |
| 6,433,001 | B1 | 8/2002 | Bach et al. |
| 10,786,483 | B2 | 9/2020 | Klein et al. |
| 11,000,506 | B2 | 5/2021 | Lewin |
| 12,383,531 | B2 | 8/2025 | Lewin |
| 2008/0096963 | A1 | 4/2008 | Jean et al. |
| 2008/0249027 | A1 | 10/2008 | Cunningham et al. |
| 2009/0234011 | A1 | 9/2009 | Goldstein |
| 2010/0204249 | A1 | 8/2010 | Hislop et al. |
| 2011/0269786 | A1 | 11/2011 | Hislop et al. |
| 2014/0087003 | A1 | 3/2014 | Cisneros |
| 2015/0224094 | A1 | 8/2015 | Lewin |

FOREIGN PATENT DOCUMENTS

| | | | |
|---|---|---|---|
| AU | 2001278602 | B2 | 12/2004 |
| CN | 109562098 | B | 4/2023 |
| EP | 3448378 | B1 | 4/2024 |
| EP | 3448378 | | 5/2024 |
| WO | 9929726 | A1 | 6/1999 |
| WO | 2005023310 | A2 | 3/2005 |

OTHER PUBLICATIONS

MX/A/2022/003739, Certificate of Grant and granted claims, IMPI (Instituto Mexicano de la Propiedad Industrial, the Mexican patent office) dated Mar. 22, 2024; with English translation (14 pages total).

Dongol et al., Hymenoptera Stings and the Acute Kidney Injury, European Medical Journal of Nephrology, vol. 1, Jul. 1, 2013, pp. 68-75. (cited during prosecution in Mexico).

Chauffe et al., Recent Developments with Lipoprotein-Associated Phospholipase A2 Inhibitors, Current Atherosclerosis Reports, vol. 12, No. 1, Jan. 2010, pp. 43-47. (cited during prosecution in Mexico).

Chemical Components of Insect Venoms, Compound Interest 2014, Available Online at: www.compoundchem.com, 2014, 1 page.

U.S. Appl. No. 62/303,647, U.S. Provisional Application No. filed on Mar. 4, 2016, 20 pages.

U.S. Appl. No. 62/308,673, U.S. Provisional Application No. filed on Mar. 15, 2016, 22 pages.

U.S. Appl. No. 62/423,693, U.S. Provisional Application No. filed on May 10, 2017, 62 pages.

U.S. Appl. No. 63/329,611, U.S. Provisional Application No. filed on Apr. 29, 2016, 22 pages.

U.S. Appl. No. 63/340,075, U.S. Provisional Application No. filed on May 23, 2016, 29 pages.

Appeal 2022-001944, Order by Patent Trial and Appeal Board (PTAB) mailed on May 21, 2024, 42 pages.

Balsinde et al., Regulation and Inhibition of Phospholipase A2, Annual Review of Pharmacology and Toxicology, vol. 39, Apr. 1999, pp. 175-189.

Boilard et al., Secreted Phospholipase A2 Inhibitors are Also Potent Blockers of Binding to the M-Type Receptor, Biochemistry, vol. 45, Oct. 2006, pp. 13203-13218.

Carvalho et al., Snake Venom PLA2s Inhibitors Isolated from Brazilian Plants: Synthetic and Natural Molecules, BioMed Research International, vol. 2013, Jan. 2013, pp. 1-8.

Clark et al., Potential Therapeutic Uses of Phospholipase A2 Inhibitors, Expert Opinion on Therapeutic Patents, vol. 14, Jul. 1, 2004, pp. 937-950.

(Continued)

*Primary Examiner* — Po-Chih Chen

(74) *Attorney, Agent, or Firm* — Kilpatrick Townsend & Stockton LLP

(57) ABSTRACT

This disclosure provides medicaments and methods for treating envenomation using small molecule inhibitors of secretory phospholipase A2 (sPLA2). The sPLA2 inhibitor AZD2716 and related compounds can be used as monotherapy. Alternatively, the sPLA2 inhibitor varespladib and/or methyl varespladib can be used in combination with a statin. When a subject has been envenomed (for example, by a snake bite or bee sting), the medicaments can be administered to prevent lethal effects or tissues damage cause by the venom: for example, acute kidney injury, mast cell degranulation, or cerebral edema. The medicaments may be contained in an automatic injection device or an injection pen to deliver an effective dose as soon as possible following envenomation.

20 Claims, 9 Drawing Sheets

(56) References Cited

OTHER PUBLICATIONS

El-Kik et al., Neutralization of Apis Mellifera Bee Venom Activities by Suramin, Toxicon, vol. 67, Mar. 2013, pp. 55-62.
European Application No. 17790643.5, Extended European Search Report mailed on Mar. 10, 2020, 9 pages.
Filho et al., Enzymatic and Structural Characterization of New PLA2 Isoform Isolated from White Venom of Crotalus Durissus Ruruima, Toxicon, vol. 53, Jan. 2009, pp. 104-114.
Folmer et al., Marine Natural Products Targeting Phospholipases A2, Biochemical Pharmacology, vol. 80, No. 12, Aug. 27, 2010, pp. 1793-1800.
Giordanetto et al., Discovery of AZD2716: A Novel Secreted Phospholipase A2 (sPLA2) Inhibitor for the Treatment of Coronary Artery Disease, American Chemical Society Medicinal Chemistry Letters, vol. 7, No. 10, Aug. 9, 2016, pp. 884-889.
Howes et al., Neutralization of the Haemorrhagic Activities of Viperine Snake Venoms and Venom Metalloproteinases Using Synthetic Peptide Inhibitors and Chelators, Toxicon, vol. 49, Apr. 2007, pp. 734-739.
Ichihara et al., Cajucarinolide and Isocajucarinolide: Anti-Inflammatory Diterpenes from Croton Cajucara, Planta Medica, vol. 58, No. 6, Dec. 1992, pp. 549-551.
Laustsen et al., From Fangs to Pharmacology: The Future of Snakebite Envenoming Therapy, Current Pharmaceutical Design, vol. 22, Jun. 2016, pp. 1-24.
Lewin et al., Varespladib (LY315920) Appears to be a Potent, Broad-Spectrum, Inhibitor of Snake Venom Phospholipase A2 and a Possible Pre-Referral Treatment for Envenomation, Toxins, vol. 8, No. 9, Aug. 25, 2016, pp. 1-16.
Magrioti et al., Phospholipase A2 Inhibitors for The Treatment of Inflammatory Diseases: A Patent Review (2010—Present), Expert Opinion on Therapeutic Patents, vol. 23, No. 3, Jan. 2013, pp. 333-344.
Marchi-Salvador et al., Crystal Structure of a Phospholipase A (2) Homolog Complexed with P-Bromophenacyl Bromide Reveals Important Structural Changes Associated with the Inhibition of Myotoxic Activity, Biochimica et Biophysica Acta, vol. 1794, Nov. 2009, pp. 1583-1590.
Marcussia et al., Snake Venom Phospholipase A2 Inhibitors: Medicinal Chemistry and Therapeutic Potential, Current Topics in Medicinal Chemistry, vol. 7, Feb. 2007, pp. 743-756.
Nicholls et al., Varespladib and Cardiovascular Events in Patients with an Acute Coronary Syndrome: the VISTA-16 Randomized Clinical Trial, The Journal of the American Medical Association, vol. 311, No. 3, Jan. 15, 2014, pp. E1-E11.
Oslund et al., Highly Specific and Broadly Potent Inhibitors of Mammalian Secreted Phospholipases A2, Journal of Medicinal Chemistry, vol. 51, Aug. 2008, pp. 4708-4714.
International Application No. PCT/US2017/030436, International Preliminary Report on Patentability mailed on Nov. 8, 2018, 9 pages.
International Application No. PCT/US2017/030436, International Search Report and Written Opinion mailed on Sep. 21, 2017, 13 pages.
Pereafiez et al., The Biflavonoid Morelloflavone Inhibits the Enzymatic and Biological Activities of a Snake Venom Phospholipase A2, Chemico-Biological Interactions, vol. 220, Sep. 2014, pp. 94-101.
Rodrigues et al., Sulfated Galactan from Palisada Flagellifera Inhibits Toxic Effects of Lachesis Muta Snake Venom, Marine Drug, vol. 13, No. 9, Jun. 11, 2015, pp. 3761-3775.
Rucavado et al., Effect of the Metalloproteinase Inhibitor Batimastat in the Systemic Toxicity Induced by Bothrops Asper Snake Venom: Understanding the Role of Metalloproteinases in Envenomation, Taxicon, vol. 43, Apr. 2004, pp. 417-424.
Samy et al., Therapeutic Application of Natural Inhibitors Against Snake Venom Phospholipase A2, Bioinformation, vol. 8, No. 1, Jan. 2012, pp. 48-57.
Song et al., Subcellular Membrane Impairment and Application of Phospholipase A2 Inhibitors in Endotoxic Shock, Injury, vol. 30, No. 1, Jan. 1999, pp. 9-14.
Sunitha et al., Neutralization of Haemorrhagic Activity of Viper Venoms by 1-(3-Dimethylaminopropyl)-1-(4-Fluorophenyl)-3-oxo-1,3-Dihydroisobenzofuran-5-Carbonitrile, Basic & Clinical Pharmacology & Toxicology, vol. 109, Oct. 2011, pp. 292-299.
Teixeira-Cruz et al., A Novel Apilic Antivenom to TreatMassive, Africanized Honeybee Attacks: A Preclinical Study from the Lethality to Some Biochemical and Pharmacological Activities Neutralization, Toxins, vol. 13, No. 30, Jan. 5, 2021, pp. 1-18.
Ticli et al., Rosmarinic Acid, a New Snake Venom Phospholipase A2 Inhibitor from Cordia Verbenacea (Boraginaceae): Antiserum Action Potentiation and Molecular Interaction, Toxicon, vol. 46, Sep. 2005, pp. 318-327.
Touaibia et al., Inhibition of Secreted Phospholipase A2. 4-Glycerol Derivatives of 4,5-Dihydro-3-(4-tetradecyloxybenzyl)-1,2,4-4H-oxadiazol-5-one with Broad Activities, Journal of Medicinal Chemistry, vol. 50, No. 7, Apr. 5, 2007, pp. 1618-1626.
Wang et al., Exploration of the Inhibitory Potential of Varespladib for Snakebite Envenomation, Molecules, vol. 23, No. 2, Feb. 2018, pp. 1-13.
Wang et al., Phospholipase A2 Inhibitor Varespladib Prevents Wasp Sting-induced Nephrotoxicity in Rats, Toxicon: Official Journal of the International Society on Toxinology, vol. 215, Jun. 11, 2022, pp. 69-76.
Wouters et al., Estimated Research and Development Investment Needed to Bring a New Medicine to Market, 2009-2018, The Journal of the American Medical Association, vol. 323, No. 9, Mar. 3, 2020, pp. 844-853.
Ciepiela et al., Flow Cytometric Osmotic Fragility Test: Increased Assay Sensitivity for Clinical Application in Pediatric Hematology, Cytometry Part B: Clinical Cytometry, vol. 94, No. 1, Jan. 2018, pp. 189-195.
Israel Application No. 307232, Notice of Allowance mailed on Aug. 21, 2025, 10 pages (3 pages of original document and 5 pages of English Translation and 2 pages of the Claims accepted for grant in Israel No. 307232).

USE OF SPLA2 INHIBITORS TO TREAT ENVENOMATION BY SNAKES AND WASPS

CROSS-REFERENCE TO RELATED APPLICATIONS

This application is a continuation of application Ser. No. 16/097,160 filed Oct. 26, 2018 (pending), which is the U.S. National Stage of PCT Application No. PCT/US2017/030436, filed May 1, 2017, which claims the priority benefit of U.S. Provisional Application No. 62/329,611, filed Apr. 29, 2016; U.S. Provisional Application No. 62/340,075, filed May 23, 2016, and U.S. Provisional Application No. 62/423,693, filed Nov. 17, 2016. All the aforesaid priority applications are hereby incorporated herein by reference in their entireties for all purposes.

FIELD OF THE INVENTION

The invention finds application in the fields of medicine and veterinary medicine.

BACKGROUND

Phospholipase A2 (PLA2) is involved in the pathology of several diseases and conditions, including envenomation (by vertebrates such as snakes and fish and invertebrates such as swarming hymenoptera, centipedes and jellyfish). Additionally, PLA2 is a factor in the pathology of deadly infectious diseases, with hemolysis and neuronal and brain swelling, such as that seen in cerebral malaria. These conditions primarily affect people living in poverty and can often occur simultaneously (e.g. malaria infection and snakebite).

Severe non-anaphylactic shock and acute kidney (AKI) reactions due to massive envenomation may occur after multiple stings by social wasps that attack in swarms and from a single snake bite. Wasp venom includes multiple components including acetylcholine, histamine, serotonin, hyaluronidase, catecholamines, histamine-releasing peptides (mastoparans), chemotactic peptides, neurotoxic kinins, and phospholipase A2. Phospholipases contribute to hemolysis and rhabdomyolysis and can lead to AKI as well as liver impairment, neuronal edema and pain, including chronic pain via direct venom toxicity and indirect mechanisms related to the victim's innate response to envenomation. See Chugh K S, Sharma B K, Singhal P C, *J Trop Med Hyg* 1976; 79:42-44 and Xuan B H et al., *Nephrol Dial Transplant* 2010; 25(4): 1146-50.

Infection with malaria (e.g. *Plasmodium falciparum*) remains prevalent in many areas of the world and is associated with severe disease and mortality, particularly in children living in sub-Saharan Africa. Cerebral malaria (CM) is a severe condition associated with parasitemia and mortality ranging from 10-60%. In addition, almost a third of pediatric CM survivors develop long-term neurological complications. Severe brain swelling seen on neuroimaging has been reported in pediatric CM. CM associated brain swelling is associated with poor outcomes in Kenyan children and is a significant predictor of mortality in Malawian children. This catastrophic disease process is associated with very high sPLA2 levels in cerebral fluids accompanying brain swelling. See Pappa et al. *Malar J.* 2015; 14:513. Hemolysis, rhabdomyelysis, neuronal and brain edema and AKI are the hallmarks of several severe disease conditions such as hymenoptera envenomation, snakebite, malaria, dengue, and trauma that can lead to death, long-term organ damage, disability, and chronic pain.

SUMMARY OF THE INVENTION

In some aspects, provided is a method that includes treating a subject who suffers from hymenoptera envenomation by administering a therapeutically effective amount of a PLA2 inhibitor. In some instances, the subject suffers from bee envenomation. In some instances, the method includes administering a therapeutically effective amount of a PLA2 inhibitor and a therapeutically effective amount of a statin. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the method includes administering the PLA2 inhibitor in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered before, as a co-formulation, or after the additional agent. In some instances the PLA2 inhibitor is administered to the subject by injection, infusion, intranasally, ocularly, orally, rectally, topically, or by inhalation. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the statin is administered orally, by injection or by intravenous infusion. In some instances, the PLA2 inhibitor and statin are administered within 6 hours of each other.

In some aspects, provided is a method that includes treating a subject who suffers from snake envenomation by administering a therapeutically effective amount of a PLA2 inhibitor in combination with a statin. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the method includes administering the PLA2 inhibitor in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered before, as a co-formulation, or after the additional agent. In some instances the PLA2 inhibitor is administered to the subject by injection, infusion, intranasally, ocularly, orally, rectally, topically, or by inhalation. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the statin is administered orally, by injection or by intravenous infusion. In some instances, the PLA2 inhibitor and statin are administered within 6 hours of each other.

In some aspects, provided is a method that includes treating subject who is at risk for or suffers from cerebral edema (brain swelling), the method including administering to the subject a composition containing a therapeutically effective amount of a PLA2 inhibitor. In some instances, the method further includes administering a therapeutically effective amount of a statin. In some instances, the cerebral edema is associated with cerebral malaria, head trauma, traumatic brain injury, ischemic or embolic stroke, or brain inflammation due to viral or bacterial infection. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered before, as a co-formulation, or after the additional agent. In some instances, the PLA2 inhibitor is administered to the subject by injection, infusion, intranasally, ocularly, orally, rectally, topically, or by inhalation. In some instances, the PLA2 inhibitor and statin are administered within 6 hours of each other.

In some aspects, provided is a method that includes treating a subject who is at risk for or suffers from neuronal edema or injury, the method including administering to the subject a composition containing a therapeutically effective amount of a PLA2 inhibitor. In some instances, the method further includes administering a therapeutically effective amount of a statin. In some instances, the neuronal edema or injury is associated with myelinolysis or axotomy. In some instances, the subject also suffers from cerebral edema. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a method that includes treating a subject who suffers from hemolysis by administering to the subject a composition containing a therapeutically effective amount of a PLA2 inhibitor. In some instances, the method further includes administering a therapeutically effective amount of a statin. In some instances, the hemolysis is caused by a hemolytic anemia, paroxysmal nocturnal hemoglobinuria (PNH), autoimmune spherocytosis, hereditary spherocytosis poisoning, severe burns, thalassemia, immunohemolytic anemia, parasitic diseases causing hemolysis (e.g. *Rickettsia* and malaria), infectious disease (e.g. hemolytic streptococcus), a metabolic or genetic disorder (e.g., G6PD deficiency, sickle cell disease), hemolytic uremic syndrome, or complement mediated hemolysis. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a method that includes reducing risk of hemolysis in a subject by administering to the subject a composition containing a therapeutically effective amount of a PLA2 inhibitor. In some instances, the method further includes administering a therapeutically effective amount of a statin. In some instances, the hemolysis is caused by a hemolytic anemia, paroxysmal nocturnal hemoglobinuria (PNH), autoimmune spherocytosis, hereditary spherocytosis poisoning, severe burns, thalassemia, immunohemolytic anemia, parasitic diseases causing hemolysis (e.g. *Rickettsia* and malaria), infectious disease (e.g. hemolytic streptococcus), a metabolic or genetic disorder (e.g., G6PD deficiency, sickle cell disease), hemolytic uremic syndrome, or complement mediated hemolysis. In some instances, the PLA2 inhibitor is varespladib, methyl-varespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a method that includes reducing hemolysis in a subject by administering to the subject a composition containing a therapeutically effective amount of a PLA2 inhibitor. In some instances, the method further includes administering a therapeutically effective amount of a statin. In some instances, the hemolysis is caused by a hemolytic anemia, paroxysmal nocturnal hemoglobinuria (PNH), autoimmune spherocytosis, hereditary spherocytosis poisoning, severe burns, thalassemia, immunohemolytic anemia, parasitic diseases causing hemolysis (e.g. *Rickettsia* and malaria), infectious disease (e.g. hemolytic streptococcus), a metabolic or genetic disorder (e.g., G6PD deficiency, sickle cell disease), hemolytic uremic syndrome, or complement mediated hemolysis. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a method that includes treating a subject who suffers from a mast cell disease, the method including administering to the subject a composition containing a therapeutically effective amount of a PLA2 inhibitor. In some instances, the method further includes administering a therapeutically effective amount of a statin. In some instances, the mast cell disease is a mast cell proliferation or degranulation disorder mastocytosis. In some instances, the PLA2 inhibitor is varespladib, methyl-varespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a method that includes treating a subject who suffers from acute kidney injury, the method including administering to the subject a composition containing a therapeutically effective amount of a PLA2 inhibitor. In some instances, the method further includes administering a therapeutically effective amount of a statin. In some instances, the acute kidney injury is all or partially due to a pigment nephropathy or venom toxicity. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the PLA2 inhibitor is administered at a dose in the range of 1 mg per kilogram patient body weight (mg/kg) to 1000 mg/kg, for a total daily dose in the range 100 mg to 1 gram. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing. In some instances, the method includes administering a therapeutically effective amount of a PLA2 inhibitor and a therapeutically effective amount of a statin. In some instances, the statin is administered orally, by injection or by intravenous infusion. In some instances, the PLA2 inhibitor is administered in combination with at least one additional agent, wherein the additional agent is a steroid, a metalloproteinase inhibitor, a serine protease inhibitor, a topical anesthetic emulsion, a spreading factor inhibitor, an anti-nausea agent, or an antibiotic. In some instances, the PLA2 inhibitor is administered to the subject by injection, infusion, intranasally, ocularly, orally, rectally, topically, or by inhalation. In some instances, the PLA2 inhibitor is administered before, as a co-formulation, or after the additional agent. In some instances, the PLA2 inhibitor and statin are administered within 6 hours of each other.

In some aspects, provided is a composition that includes a co-formulation of a statin and a PLA2 inhibitor. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing.

In some aspects, provided is a kit that includes a statin and a PLA2 inhibitor. In some instances, the PLA2 inhibitor is varespladib, methylvarespladib, LY433771, indoxam, methyl indoxam, 3-(5'-Benzyl-2'-carbamoylbiphenyl-3-yl) propanoic acid (Compound 4), AZD2716, a pharmaceutically acceptable salt of any of the foregoing, or combinations of any of the foregoing. In some instances, the statin is atorvastatin, cerivastatin, fluvastatin, lovastatin, a monacolin, mevastatin, pitavastatin, pravastatin, rosuvastatin, simvastatin, a pharmaceutically acceptable salt of any of the foregoing, or combinations of any of the foregoing.

In some aspects, provided is a method of using a PLA2 inhibitor, optionally in combination with a statin, for treatment of hymenoptera or other invertebrate envenomation.

In some aspects, provided is a method of using a PLA2 inhibitor in combination with a statin for treatment of snake envenomation.

In some aspects, provided is a method of using a PLA2 inhibitor, optionally in combination with a statin, for treatment of cerebral edema, neuronal edema, hemolysis, mast cell disease, or acute kidney injury.

DETAILED DESCRIPTION

Definitions

Figure 1:
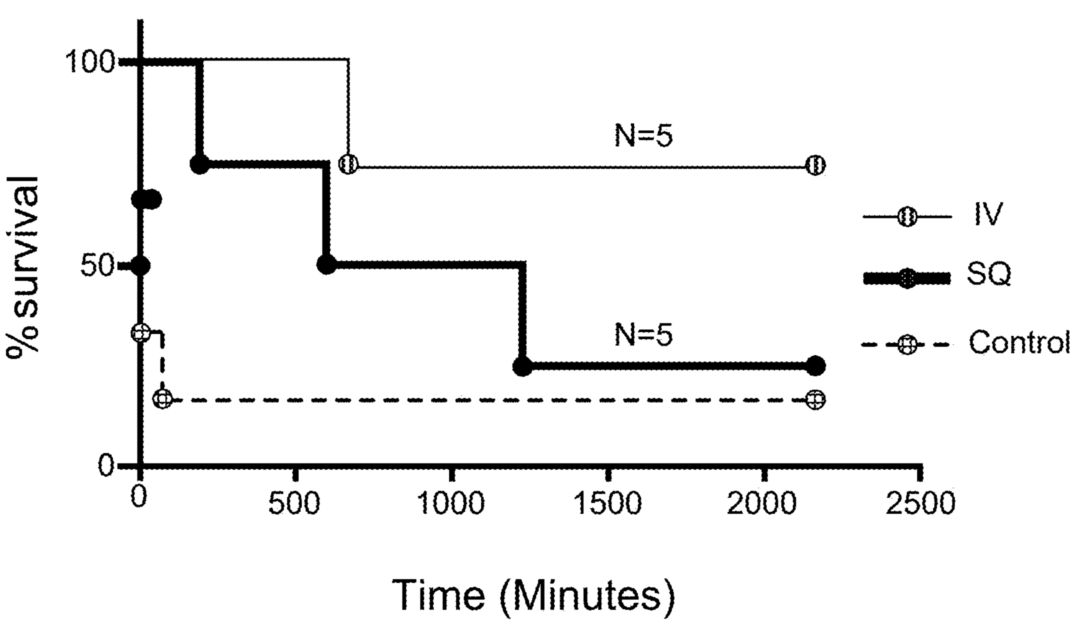
FIG. 1 shows the survival of mice treated with varespladib following exposure to lethal concentrations of bee venom. See Example 2, below.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents that form stable bonds are to be used.

As used herein and in the appended claims, the singular forms "a," "and" and "the" include plural references unless the context clearly dictates otherwise.

As used herein, "AChE" is an abbreviation for acetylcholine; "AChEI" is an abbreviation for acetylcholinesterase inhibitor; "mAChR" is an abbreviation for muscarinic acetylcholine receptor; "nAChR" is an abbreviation for nicotinic acetylcholine receptor. Inhibitors of AChE may also inhibit butyryl cholinesterases (BChE), pseudocholinesterases. "MP" is an abbreviation for metalloproteinase (e.g., mammalian matrix metalloproteinase, MMPs, "SP" is an abbreviation for serine proteases; "MPI is an abbreviation for metalloproteinase inhibitor; "SPI" is an abbreviation for serine protease inhibitor.

PLA2 is an abbreviation for phospholipase A2. PLA2-1 is an abbreviation for a PLA2 inhibitor. As used herein, in the context of venoms (e.g., hymenoptera venoms) "PLA2" and "sPLA2" are used interchangeably.

The term "patient" or "subject" or "victim" is used throughout the specification within context to describe an animal, generally a mammal, especially including a domesticated animal (e.g., dog, cat, cow, horse, sheep, goat, etc.) and preferably a human, to whom treatment, including prophylactic treatment (prophylaxis), with the compounds or compositions according to the present invention is provided. For treatment of those conditions or disease states that are specific for a specific animal such as a human patient, the term patient or subject or victim refers to that specific animal.

The term "effective" is used herein, unless otherwise indicated, to describe an amount of a compound or component which, when used within the context of its use, produces or effects an intended result, whether that result relates to the prophylaxis and/or therapy of an envenomation and/or disease state or conditions/symptom as otherwise described herein. The term effective subsumes all other effective amount or effective concentration terms (including the term "therapeutically effective") that are otherwise described or used in the present application. The term effective also includes periods of administration whether such administration represents a single administration, often orally or by injection or a single administration followed by hours, days or weeks of supplemental administration to a point where the administration is stopped because of clearance of the venom from the patient or the decision to institute alternative therapy, including the administration of a traditional serum-derived anti-venom composition.

As used herein, a "therapeutically effective amount" of a drug (e.g., PLA2 inhibitor) is an amount of a drug that, when administered to a subject with a medical condition (e.g., snake envenomation, hymenoptera envenomation, cerebral edema, neuronal edema or injury, hemolysis, mast cell disease, acute kidney injury), will have the intended therapeutic effect, e.g., alleviation, amelioration, palliation or elimination of one or more manifestations of the condition in the subject. The full therapeutic effect does not necessarily occur by administration of one dose, and may occur only after administration of a series of doses. Thus, a therapeutically effective amount may be administered in one or more administrations.

The term "compound" is used herein to describe any specific compound or bioactive agent disclosed herein, including any and all stereoisomers (including diastereomers), individual optical isomers (enantiomers) or racemic mixtures, pharmaceutically acceptable salts including alternative pharmaceutically acceptable salts, prodrug forms and deuterated or other isotopic substitutions. The term compound herein refers to stable compounds. Within its use in context, the term compound may refer to a single compound or a mixture of compounds as otherwise described herein. Compounds for use in the present invention may also include hydrates, solvates and/or polymorphs of the individual compounds. When a bioactive agent is disclosed for use in the present invention, it is understood that such term within the context of its use includes its pharmaceutically acceptable salts and/or alternative pharmaceutically acceptable salts unless specifically stated otherwise.

Varespladib is ((3-(2-Amino-1,2-dioxoethyl)-2-ethyl-1-(phenylmethyl)-1H-indol-4-yl)oxy) acetic acid.

Methylvarespladib, or LY433771, is {9-[(phenyl) methyl]-5-carbamoylcarbazol-4-yl}oxyacetic acid.

AZD2716 is [1,1'-Biphenyl]-3-propanoic acid, 2'-(aminocarbonyl)-α-methyl-5'-(phenylmethyl)-,(αR)—(R)-7 (CAS 1845753-81-2).

Compound 4 or "Comp. 4" is 3-(5'-Benzyl-2'-carbamoylbiphenyl-3-yl) propanoic acid.

A "statin" is a HMG-CoA reductase inhibitor. As used herein "statin" generally refers to inhibitors useful for human or veterinary use.

Hymenoptera (or swarming hymenoptera) include bees, wasps, and ants.

Bee refers to members of the *Apis* and related genera.

Venomous invertebrates includes, but are not limited to, scorpions, spiders, insects, cnidarian, myriapods and mollusks and includes poisonous caterpillars.

"Venom" has its normal meaning and is a poisonous secretion or substance from an animal, such as an insect (e.g., hymenoptera, such as bees, wasps and ants), snakes, or venomous vertebrates or invertebrates injected into the victim by bite, sting, or other mode of injection or contact.

Hymenoptera venoms are venoms from Hymenoptera. Hymenoptera venom is generally composed of proteins, peptides, and vasoactive amines, which can collectively cause the toxic properties of insect bites and stings.

As used herein "envenomation," refers to injection of venom into a victim as a result of a bite or sting by a venomous arthropod (e.g. bees, wasps, ants or scorpion) or other invertebrate (e.g. cnidarian) or vertebrate such as a snake or fish.

50 or $LD_{50}$ designates the estimated dose or level of exposure at which approximately 50% of exposed subjects will die as a result of that exposure (e.g. venom or toxin dose).

Swarming Hymenoptera envenomation means exposure to venom from swarming Hymenoptera Bee envenomation means exposure to venom from bees.

Venomous invertebrate envomation means exposure to venom from venomous invertebrates such as scorpions, spiders, insects, cnidarian, myriapods and mollusks and includes poisonous caterpillars.

The terms "treat", "treating", and "treatment", are used synonymously to refer to any action providing a benefit to a patient at risk for or suffering from an envenomation, including improvement in the condition through lessening, inhibition, suppression or elimination of at least one symptom, delay in progression of or damage from the envenomation or related disease, prevention, delay in or inhibition of the likelihood of the onset of envenomation symptoms, etc.

"Storage-stable" in reference to a drug formulation means there is less than 10% degradation when for a specified period of time at a specified temperature (e.g. 18 months at 25° C.).

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

The term "small molecule" as used herein, refers to a molecule with a molecular weight of less than about 2500, or less than about 1000, or less than about 750, or less than about 500.

The term "co-administration" is used to describe the administration of two or more active compounds in effective amounts. Although the term co-administration preferably includes the administration of two or more active compounds to the patient at about the same time (simultaneous, concurrently, or sequentially on the same day, within 12 hours of each other, within 6 hours of each other or within 1 hour of each other), it is not necessary that the compounds actually be administered at exactly the same time (simultaneous) or even close in time (concurrent/sequential), only that amounts of compound will be administered to a patient or subject such that effective concentrations are found in the blood, serum or plasma, or in the pulmonary tissue at the same time to produce an intended result.

The term "co-formulation" refers to more than one active compound being formulated into a single dosage form for administration to the patient in that single dosage form.

The term antibody or anti-venom refers to monoclonal, polyclonal, monovalent, polyvalent or combinations of whole or fragmented IgG, IgM, IgE, or IgA antibodies from any source.

Overview

As detailed herein, it has been discovered that, surprisingly, administration of a PLA2 inhibitor to a subject suffering from hymenoptera envenomation may be treated by administering a therapeutically effective amount of a PLA2 inhibitor. A statin may be co-administered.

As detailed herein, it has been discovered that, surprisingly, administration of a PLA2 inhibitor to a subject suffering from hymenoptera envenomation can be successfully treated at the same doses used to treat snakebite. In some instances, the statin can, surprisingly, also inhibit some venom activity and may be co-administered with a PLA2 inhibitor and improve its potency against snake venom.

Also disclosed herein is the use of a PLA2 inhibitor, optionally in combination with a statin, for treatment of a condition secondary to envenomation (e.g. venom-induced acute kidney injury and/or cardiomyopathy associated with snake and bee envenomation).

Also disclosed herein is the use of a PLA2 inhibitor, optionally in combination with a statin, for treatment of conditions associated with hemolysis.

Also disclosed herein is the use of a PLA2 inhibitor, optionally in combination with a statin, for treatment of to treat conditions associated with cerebral and neuronal edema (e.g. for treatment of events triggering or characterized by brain swelling, myelinolysis or axotomy).

Also disclosed herein is the use of a PLA2 inhibitor, optionally in combination with a statin, for treatment of patients in need of neuroprotection, including the development of neuropathic pain.

PLA2 inhibitors, optionally in combination with a statin, may be combined with stored blood products to improve the stability of blood storage and reduce the need or substitute for cyclosporine in the setting of angioedema and inflammatory disorders such as rheumatoid arthritis.

Furthermore, victims of a bee or other swarming hymenoptera sting with a mast cell proliferation or degranulation disorder, or hemolysis are envisioned to further benefit from a broad-spectrum venom antidote, such as PLA2, in the setting of envenomation.

1. Administration of a PLA2 Inhibitor to Treat Hymenoptera (e.g. Bee) Envenomation Previous work by the inventor demonstrated that administration of PLA2 inhibitors was protective or curative against the effects of snake evenomation. See PCT publication WO2016081826A2 and in Lewin M, et al., 2016, "Varespladib (LY315920) Appears to Be a Potent, Broad-Spectrum, Inhibitor of Snake Venom Phospholipase A2 and a Possible Pre-Referral Treatment for Envenomation" *Toxins* 248:8, both incorporated by reference herein. In these studies, PLA2 inhibitors (varespladib and methyl-varespladib) performed extremely poorly when tested in vitro against bee venom sPLA2, exemplified by the high $IC_{50}$ (μm) using validated assays for PLA2 inhibition. Surprisingly, it has now been discovered that PLA2 inhibitors are effective against lethal doses of bee venom in vivo and prevent KAI from bee venom. See Example 2, below. This discovery indicates that PLA2 inhibitors may be used for field-treatment for non-anaphylactic shock due to swarming hymenoptera, and because of the multiple administration mechanisms available for PLA2 inhibitors and combinations thereof, life and organ-sparing interventions are possible in both out-of-hospital and hospital settings.

The inventor previously identified pharmaceutical compositions, systems and kits that rapidly and effectively treat envenomation-damaged tissue and a broad spectrum of their associated sequelae, most significantly, immediate life-threating from venom-induced shock, neurological, hematological and renal catastrophe from hemolytic and other hemotoxic processes. Specifically, the inventor discovered that the use of a PLA2 inhibitor was effective against numerous differing types of snake venom PLA2s, irrespective of snake species. The methods and concepts relating to snake venom treatment with PLA2 inhibitors are further discussed in WO2016081826A2 and Lewin M, et al. 2016 *Toxins* 248:8.

In these previous studies, experimentation using a spectrum of snake venoms demonstrated a correlation of the effects of PLA2 inhibitors (e.g. varespladib and methyl-varespladib) in vitro on snake venom and in vivo protection or rescue treatment in mice and rats. The real-time, in vivo blood sampling results demonstrating PLA2 inhibition by activity assays correlated with increased survival of rodents to whom snake venom was administered followed by a therapeutic dose of PLA2 inhibitor. However, as shown in the earlier studies, PLA2 inhibitors performed poorly or not-at-all when tested in vitro against bee venom sPLA2. Furthermore, the academic literature reports that the type of PLA2 found in bee venom is Type 11 or "atypical" and frequently-utilized PLA2 inhibitory compounds do not inhibit bee venom sPLA2. See e.g. Murakami M, et al. 2015 *J. Lipid. Res.* 56:1248-1261.

Despite the previously-observed, very weak or completely absent activity of PLA2 inhibitors against bee venom, here the inventor reports the unexpected discovery that PLA2 inhibitors are protective or curative against otherwise lethal doses of bee venom in vivo. See Example 1, TABLE 1 and FIG. 1. This discovery was completely unexpected in view of the in vitro 5-45,000 fold higher $IC_{50}$ of LY315920 and up to >100,000 times higher than methyl-varespladib and Compound 4 against bee venom PLA2 as compared to snake venom PLA2. Based on in vitro data, administering a clinically useful or safe amount of PLA2 inhibitor effective against bee venom would have been impossible.

The surprising finding of the in vivo efficacy of PLA2 inhibitors against bee venom may lead to the development of the first ever field-treatment for severe bee sting and non-anaphylactic shock due to solitary or swarming hymenoptera. Significantly, there are no anti-sera for hymenoptera stings and a pharmacological intervention is highly desired in places where swarm behavior is a risk or for patients with high-risk sensitivity such as anaphylactic, anaphylactoid, or large local reactions due to invertebrate envenomation. Pharmaceutical compositions and kits containing such compositions according to the present invention, unlike anti-venom, will more readily penetrate through tissues effecting rapid and favorable results. The present invention addresses the limitations of standard therapies and in certain embodiments, when combined with standard therapy as first-line therapy or co-formulation, renders standard therapies far more effective than when used alone.

Embodiments of the present disclosure can further extend to methods of treatment comprising at least one PLA2 inhibitor in combination with one or more agents/compositions presented herein. Together these agents provide methods and compositions for treating or reducing the likelihood of tissue damage, acute kidney injury, bleeding and clotting disorders, cardiovascular collapse or neurotoxin-induced respiratory failure and long-lasting neuronal damage (e.g. neuropapathic pain) resulting from hymenoptera stings and other types of envenomation.

In one aspect, administration of a PLA2 inhibitor is used to treat Large Local Reactions (LLRs) in hymenoptera sting, and non-venom induced types of angioedema as well as reduce the release and effects of histamine.

2. Co-Administration of a PLA2 Inhibitor and a Statin

Statins are drugs widely used to reduce cholesterol levels associated with low-density lipoproteins (LDL). See Example 4. An effect of envenomation is hemolysis. It has also been discovered that statins in combination with some PLA2 inhibitors reduced hemolysis to a greater degree than PLA2 inhibitor alone.

The combination of a PLA2 inhibitor and a statin may be used to treat any of the conditions described herein for which administration of a PLA2 inhibitor alone provides benefit. These conditions include hymenoptera (e.g. bee) envenomation, snake envenomation-induced kidney or cerebral damage, conditions associated with hemolysis and conditions associated with cerebral edema, especially cerebral malaria or axonal damage such as axonal myelinolysis and neuropathic pain from axonal damage.

The discovery of such benefit results from the combination of PLA2 inhibitors and statins demonstrates a previously uncharacterized link between cholesterol metabolism and the effects of venom. The effects of envenomation and malaria, especially cerebral malaria, are sweeping problems in the developing world and increasingly, in the developed world; a common treatment for both diseases would represent a monumental advancement of human health.

3. Administration of a PLA2 Inhibitor to Treat Conditions Associated with Hemolysis The discovery that treatment with PLA2 inhibitors (alone or in combination with a statins) is effective in reducing hemolysis from multiple causes. See Example 2 and FIG. 1-3.

As detailed herein, it has been discovered that, surprisingly PLA2 inhibitors with and without statins have general anti-hemolytic properties, and that administration of a PLA2 inhibitor, optionally in combination with a statin, to a subject suffering from a condition characterized by abnormal hemolysis or osmotic frailty reduces hemolysis. This unexpected finding suggests that there is a general therapeutic potential for PLA2 inhibitors alone or, especially, in combination with statins to treat hemolytic anemias, paroxysmal nocturnal hemoglobinuria (PNH) or diseases or conditions associated with osmotic fragility, including but not limited to autoimmune spherocytosis, hereditary spherocytosis poisoning, severe burns, thalassemia, immunohemolytic anemia, and parasitic diseases causing hemolysis (e.g. *Rickettsia*-induced hemolysis and malaria).

4. Administration of a PLA2 Inhibitor for Neuroprotection and to Treat Conditions Associated with Cerebral Edema A common sign of severe envenomation is cerebral edema (brain swelling) and neuronal edema (e.g. spinal cord or peripheral nerve/nerve-terminal swelling and destruction). The swelling is reduced by blocking PLA2 activity (data not shown). The methods disclosed herein further relate to a method of treating conditions associated with brain swelling (including envenomation) wherein treatment of a patient with a therapeutically effective amount of a composition according to the present invention, comprising administering at least one PLA2 inhibitor compound to the patient.

In one aspect, the condition associated with edema is hymenoptera stings.

In one aspect, the condition associated with edema and requiring neuroprotection is cerebral malaria or trauma causing cerebral swelling (e.g. blunt trauma or peripheral nerve axotomy or spinal cord myelinolysis).

Embodiments of the present disclosure can further extend to methods of treatment comprising at least one PLA2 inhibitor in combination with one or more agents/compositions presented herein. Together these agents provides a method for treating or reducing the likelihood of tissue damage, bleeding and clotting disorders, cardiovascular collapse or neurotoxin-induced respiratory failure resulting from hymenoptera stings and other brain swelling.

5. Administration of a PLA2 Inhibitor to Preserve Blood Pressure and Kidney Function in a Patient with Anaphylactic or Non-Anaphylactic Shock A PLA2 inhibitor with or without a statin would prove advantageous for the preservation of blood pressure and kidney function in the settings of venom-induced shock and acute kidney injury.

6. Use of PLA2 Inhibitors to Reduce Hemolysis of Blood Products

In one aspect, a PLA2 inhibitor is combined with blood or blood products undergoing centrifugation, prolonged storage or mechanical stress.

Phospholipase A2

Lipases are enzymes that release biologically active molecules from membrane lipids. A key lipase enzyme family consists of phospholipase A2 (PLA2). PLA2 catalyzes the hydrolysis of phospholipids at the sn-2 position yielding a free fatty acid and a lysophospholipid. PLA2 contributes towards release and/or formation of at least three important lipid mediators from membrane-arachidonic acid, platelet activating factor and lysophosphatidic acid or lysophosphatidylcholine inducing inflammatory responses and red blood cell rupture and splenic destruction by increased presentation of phosphatidyl-serine. The release of arachidonic acid from membrane phospholipids by PLA is believed to be a key step in the control of eicosanoid production within the cell. PLA2 enzymes are usually grouped into cytosolic PLA2 (cPLA2), secretory PLA2 (sPLA2) and calcium independent PLA2 (iPLA2). Venom (e.g. bee venom) PLA2 are secreted (i.e., sPLA2s). Classification of PLA2s is based on molecular weight, calcium requirement, structural features, substrate specificity and functional role. See Ray, et al., “Phospholipase A2 in Airway Disease: Target for Drug Discovery,” Journal of Drug Discovery and Therapeutics 1 (8) 2013, 28-40. Conventionally, Groups I/1/V/X are classified as ‘conventional’ sPLA2s, and Types Ill and XII are classified as ‘atypical’ sPLA2s. See e.g. Murakami, M et al. A new era of secreted phospholipase A2 2015 *J. Lipid. Res.* 56:1248-1261, and Murakami, M and Taketomi, Y 2015 *Allergology Int’l* 64:4-10, each incorporated herein by reference.

PLA2 Inhibitors

PLA2 inhibitors have been identified in plants, venom, and other sources. PLA2 inhibitors have been investigated as potential therapeutic agents for treatment of inflammatory diseases. See, e.g. Magrioti, V, and Kokoto, G. *Expert opinion on therapeutic patents* 20.1 (2010): 1-18); and Dennis, Edward A., et al. *Chemical reviews* 111.10 (2011): 6130-6185, each incorporated herein by reference. However, no small molecule PLA2 inhibitors have been approved as agents for treating acutely life-threatening illnesses or conditions. PLA2 inhibitors are further discussed in PCT publication WO2016081826A2, incorporated herein by reference.

Although venoms may contain PLA2, without intending to be bound by a specific mechanism, the effects of the PLA2 inhibitors used according to the invention may be mediated by inhibition of host PLA2s or by inhibition of both host and venom PLAs. In some embodiments of the present invention, the PLA2 inhibitor is not specific for venom or parasite PLA2 but has inhibitory activity against both mammalian (e.g. human, mouse or rat) PLA2 and venom PLA2 or only mammalian PLA2. Without intending to be bound by a specific mechanism, the efficacy of the PLA2 inhibitor (e.g., varespladib, methylvarespladib (indoles), LY433771 (a carbazole), Compound 4 and related compounds e.g. AZD2716 (pyrazoles)) may result from the dual inhibition of host (mammalian or human) PLA2 activity, reducing the host's production of C-reactive protein and reducing an overall inflammatory response, as well as venom PLA2 activity thereby reducing the propensity to develop pathological cascades associated with tissue damage, consumption coagulopathy and other toxic cascades induced by the venom or parasite. In some instances, the efficacy of the PLA2 inhibitor may result primarily to inhibition of the host PLA2 response.

In some embodiments, the treatment comprises at least one PLA2 inhibitor, preferably selected from varespladib, methylvarespladib, LY433771, Compound 4, or AZD2716. In some embodiments a combination of two or more than two different PLA2 inhibitors are administered. In some embodiments, the PLA2 inhibitor(s) is administered in combination with other pharmaceutically active agents, or in specific formulations, as described herein. In some embodiments the PLA2 inhibitor(s) is administered in combination with a statin.

In some embodiments the PLA2 inhibitor is a small molecule (e.g., MW<2000, <1000, or <500). PLA2 inhibitors for use herein include varespladib, the chemical structure of which is presented below:

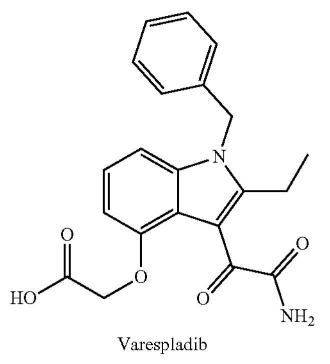 [SMILES: CCc1c(C(=O)C(N)=O)c2c(OCC(=O)O)cccc2n1Cc1ccccc1]

Varespladib

PLA2 inhibitors for use herein include methylvarespladib, the chemical structure of which is presented below:

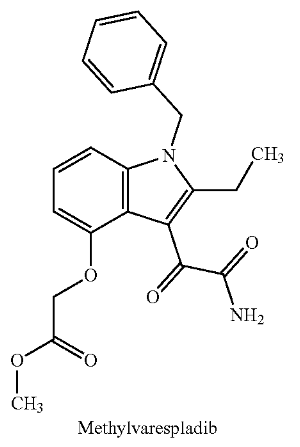 [SMILES: CCc1c(C(=O)C(N)=O)c2c(OCC(=O)OC)cccc2n1Cc1ccccc1]

Methylvarespladib

PLA2 inhibitors for use herein include LY43371, the chemical structure of which is presented below:

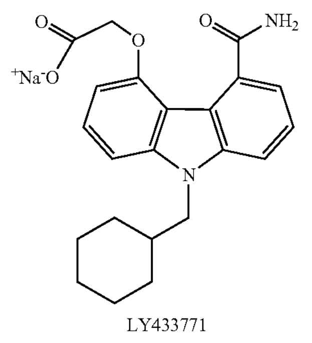

LY433771

PLA2 inhibitors for use herein include Compound 4 or the related structure, AZD2716. These structures differ by a methyl group; Compound 4 is racemic, whereas AZD2716 is the R-stereoisomer of the methylated version of Compound 4. See Giordanetto, F., et al., *ACS Med. Chem. Lett.* 2016:7, 884-889. The chemical structure of AZD2716 is presented below:

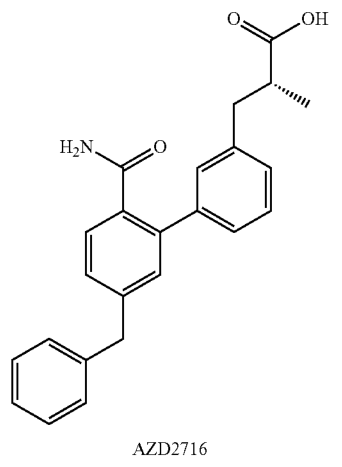 [SMILES: C[C@H](Cc1cccc(-c2cc(Cc3ccccc3)ccc2C(N)=O)c1)C(=O)O]

AZD2716

PLA2 inhibitors for use herein include indoxam, the chemical structure of which is presented below:

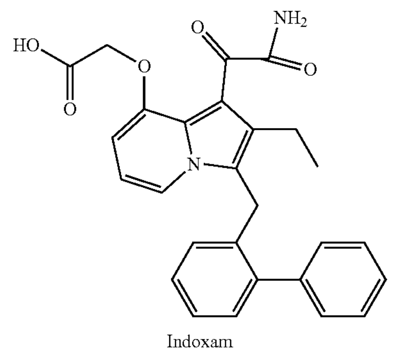 [SMILES: CCc1c(C(=O)C(N)=O)c2c(OCC(=O)O)cccn2c1Cc1ccccc1-c1ccccc1]

Indoxam

PLA2 inhibitors for use herein include methyl indoxam ("Me-indoxam"), the chemical structure of which is presented below:

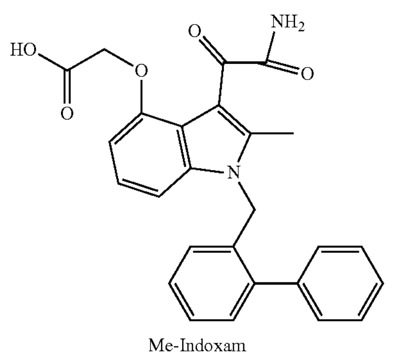 [SMILES: Cc1c(C(=O)C(N)=O)c2c(OCC(=O)O)cccc2n1Cc1ccccc1-c1ccccc1]

Me-Indoxam

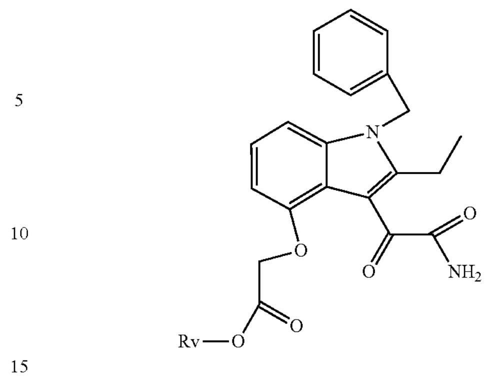

Other PLA2 inhibitors, such as but not limited to other 1H-indole-3-glyoxylamides, are also useful in treatment of envenomation and brain swelling include the carbazoles related to LY433771 and optionally, Compound 4 or AZD2716.

PLA2 inhibitors for use herein include 4-benzyl-benzamide; 5'-Benzyl-2'-carbamoylbiphenyl-3-carboxylic acid; 2-(5'-Benzyl-2'-carbamoylbiphenyl-3-yl)acetic acid; 3-(5'-Benzyl-2'-carbamoylbiphenyl-3-yl)propanoic acid (Compound 4); 4-(5'-benzyl-2'-carbamoylbiphenyl-3-yl)butanoic acid; 2-(5'-Benzyl-2'-carbamoylbiphenyl-3-yloxy)acetic acid; 3-(5'-Benzyl-2'-carbamoylbiphenyl-3-yl)-2-methylpropanoic acid; 2-((5'-Benzyl-2'-carbamoylbiphenyl-3-yl)methyl)butanoic acid; and 1-((5'-benzyl-2'-carbamoylbiphenyl-3-yl)methyl)cyclopropanecarboxylic acid.

Additional PLA2 inhibitors include those described in U.S. Pat. No. 5,654,326, including compounds according to the chemical structure:

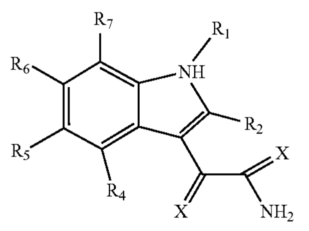

where X is O or S, preferably 0;

R1 is C7-C20 alkyl, C7-C20 alkenyl, C7-C20 alkynyl, a carbocyclic radical (preferably a benzyl or ethylphenyl group) or a heterocyclic radical;

R2 is hydrogen, halo (F, Cl, Br, I), C1-C3 alkyl (preferably ethyl) or C3-C4 cycloalkyl;

R4 is H or an —O—(CH2)m-C(O)ORv group, where m is 1-3 (preferably 1) and Rv is H or a C1-C3 alkyl group, preferably CH3; and R5, R6 and R7 are H, Or a pharmaceutically acceptable salt, solvate or polymorph thereof.

PLA2 inhibitor compounds (varespladib and methylvarespladib) for use in the present invention may also be represented by the chemical structure:

where Rv is H (varespladib) or methyl (methylvarespladib), or their pharmaceutically acceptable salts. The above compounds also may be used as prodrug forms C1-C6 alkyl esters, C2-C7 acyloxyalkyl esters, or C3-C9 alkyloxycarbonyloxyalkyl esters (each formed at R4). These and other related compounds for use in the present invention are described in U.S. Pat. No. 5,654,326.

Additional PLA2 inhibitors include for example: Varespladib Mofetil, N-Acetyl Cysteine, LY329722 (sodium [3-aminooxyalyl-1-benzyl-2-ethyl-6-methyl-1H-indol-4-yloxy]-acetic acid), ochnaflavone (a naturally occurring biflavonoid), BPPA (5-(4-benzyloxyphenyl)-4S-(7-phenylhepatonoylamino) pentanoic acid, and p-bromophenacylbromide (p-BPB) and other benzophenone oximes derivatized with syndone. In certain embodiments, PLA2 inhibitors for use in the current invention are selected from the group consisting of: {9-[(phenyl)methyl]-5-carbamoylcarbazol-4-yl}oxyacetic acid; θ-benzyl-δJ-dimethoxy-S-tetrahydrocarbazole-carboxylic acid hydrazide; 9-benzyl-5,7-dimethoxy-1,2,3,4-tetrahydrocarbazole-4-carboxamide; [9-benzyl-4-carbamoyl-7-methoxy-1,2,3,4-tetrahydrocarbazol-5-yl]oxyacetic acid; [9-benzyl-4-carbamoyl-7-methoxycarbazol-5-yl]oxyacetic acid; methyl [9-benzyl-4-carbamoyl-7-methoxycarbazol-5-yl]oxyacetic acid; 9-benzyl-7-methoxy-5-cyanomethyloxy-S-tetrahydrocarbazole-carboxamide; 9-benzyl-7-methoxy-5-(1H-tetrazol-5-yl-methyl)oxy)-1,2,3,4-tetrahydrocarbazole-4-carboxamide; {9-[(phenyl)methyl]-5-carbamoyl-2-methyl-carbazol-4-yl}oxyacetic acid; {9-[(3-fluorophenyl)methyl]-5-carbamoyl-2-methylcarbazol-4-yl}oxyacetic acid; {9-[(3-methylphenyl)methyl]-5-carbamoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1, 2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido) ethyloxy-2-methoxycarbazole-5-carboxamide; 9-benzyl-5-methanesulfonamidoylmethyloxy-7-methoxy-1, 2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl) carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethyllcarbazol^-ylloxyacetic acid; [5-carbamoyl-2-phenyl-9-(phenylmethyl)carbazol-4-yl]oxyacetic acid; [5-carbamoyl-2-(4-chlorophenyl)-9-(phenylmethyl) carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethylJsilyOoxymethyllcarbazol^-ylloxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(1-naphthyljmethyll-5-carbamoylcarbazol^-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(3,5-dimethylphenyl)methyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl}oxyacetic acid; {9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(2-biphenyl)methyl]-5-carbamoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazol-5-yl]oxyacetic acid; {9-[(2-Pyridyl)methyl]-5-carbamoylcarbazol-4-yl}oxyacetic acid; {9-[(3-Pyridyl)nnethyl]-5-carbannoylcarbazol-4-yl}oxyacetic acid; [9-benzyl-4-carbamoyl-8-nnethyl-1,2,3,4-tetrahydrocarbazol-5-yl]oxyacetic acid; [9-benzyl-5-carbamoyl-1-methylcarbazol-4-yl]oxyacetic acid; [9-benzyl-4-carbamoyl-8-fluoro-1,2,3,4-tetrahydrocarbazol-5-yl]oxyacetic acid; [9-benzyl-4-carbamoyl-8-chloro-1,2,3,4-tetrahydrocarbazol-5-yl]oxyacetic acid; [5-carbamoyl-9-(phenylmethyl)-2-[[(propen-3-yl)oxy]methyl]carbazol-4-yl]oxyacetic acid; [5-carbamoyl-9-(phenylmethyl)-2-[(propyloxyjmethyllcarbazolylloxyacetic acid; 9-benzyl-7-methoxy-5-((carboxamidonnethyloxy-tetrahydrocarbazole-carboxamide; 9-benzyl-7-methoxy-S-cyanonnethyloxy-carbazole-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; {9-[(phenyl)methyl]-5-carbannoyl-2-nnethyl-carbazol-4-yl}oxyacetic acid; {9-[(3-fluorophenyl)methyl]-5-carbannoyl-2-nnethylcarbazol-4-yl}oxyacetic acid; {9-[(3-methylphenyl)nnethyl]-5-carbannoyl-2-nnethylcarbazol-4-yljoxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido)ethyloxy-2-methoxycarbazole-5-carboxamide; 9-benzyl-5-methanesulfonamidoylmethyloxy-7-methoxy-1,2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl)carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethylIcarbazolyloxyacetic acid; [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethylJsilyOoxymethyll-carbazol-ylloxyacetic acid; {9-[(3-fluorophenyl)methyl]-5-carbamoylcarbazol-4-yl}oxyacetic acid; {9-[(3-chlorophenyl)methyl]-5-carbamoylcarbazol-4-yl}oxyacetic acid; {9-[(3-phenoxyphenyl)methyl]-5-carbamoylcarbazol-4-yl}oxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(3-trifluoromethylphenyl)methyl]-5-carbamoylcarbazol-4-yl}oxyacetic acid; {9-[(1-naphthyljmethyll-5-carbamoylcarbazol-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(2-methylphenyl)nnethyl]-5-carbannoylcarbazol-4-yl}oxyacetic acid; {9-[(3-methylphenyl)nnethyl]-5-carbannoylcarbazol-4-yl}oxyacetic acid; {9-[(3,5-dimethylphenyl)nnethyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl}oxyacetic acid; {9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(3-trifluoromethoxyphenyl)nnethyl]-5-carbannoylcarbazol-4-yl}oxyacetic acid; {9-[(2-biphenyl)methyl]-5-carbannoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazole-5-yl]oxyacetic acid; {9-[(2-Pyridyl)methyl]-5-carbamoylcarbazol-4-yl}oxyacetic acid; {9-[(3-Pyridyl)nnethyl]-5-carbannoylcarbazol-4-yl}oxyacetic acid; [9-benzyl-4-carbamoyl-8-nnethyl-1,2,3,4-tetrahydrocarbazol-5-yl]oxyacetic acid; [9-benzyl-5-carbamoyl-1-methylcarbazol-4-yl]oxyacetic acid; [θ-benzyl^-carbamoyl-δ-fluoro-1,2,3,4-tetrahydrocarbazol-5-yl]oxyacetic acid; [θ-benzyl-5-carbannoyl-1-fluorocarbazol-4-yl]oxyacetic acid; [9-benzyl-4-carbamoyl-8-chloro-1,2,3,4-tetrahydrocarbazol-5-yl]oxyacetic acid; [9-benzyl-5-carbamoyl-1-chlorocarbazol-4-yl]oxyacetic acid; [9-[(Cyclohexyl)methyl]-5-carbannoylcarbazol-4-yl]oxyacetic acid; [9-[(Cyclopentyl)methyl]-5-carbamoylcarbazol-4-yl]oxyacetic acid; [5-carbamoyl-9-(phenylmethyl)-2-(2-thienyl)carbazol-4-yl]oxyacetic acid; [5-carbamoyl-9-(phenylnnethyl)-2-[[(propen-3-yl)oxy]methyl]carbazol-4-yl]oxyacetic acid; [5-carbamoyl-9-(phenylnnethyl)-2-[(propyloxyjmethyllcarbazolylloxyacetic acid; 9-benzyl-7-methoxy-5-((carboxamidomethyloxy-tetrahydrocarbazole-carboxamide; 9-benzyl-7-methoxy-5-cyanomethyloxy-carbazole-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; (R,S)-(9-benzyl-4-carbamoyl-1-oxo-3-thia-1,2,3,4-tetrahydrocarbazol-5-yl)oxyacetic acid; (R,S)-(9-benzyl-4-carbamoyl-3-thia-1,2,3,4-tetrahydrocarbazol-5-yl)oxyacetic acid; 2-(4-oxo-5-carboxamido-9-benzyl-9/-/-pyrido[3,4-ib]indolyl)acetic acid chloride; [N-benzyl-1-carbamoyl-1-aza-1,2,3,4-tetrahydrocarbazol-8-yl]oxyacetic acid; 4-methoxy-6-methoxycarbonyl-10-phenylmethyl-6,7,8,9-tetrahydropyrido[1,2-a]indole; (4-carboxamido-9-phenylmethyl-4,5-dihydrothiopyrano[3,4-b]indol-5-yl)oxyacetic acid; 3,4-dihydro-4-carboxamidol-5-methoxy-9-phenylmethylpyrano[3,4-ib]indole; 2-[(2,9 bis-benzyl-4-carbamoyl-i,2,3,4-tetrahydro-betacarbolin-5-yl)oxy]acetic acid; 2-[4-oxo-5-carboxamido-9-(2-methylbenzyl)-9/-/-pyrido[3,4-ib]indolyl]acetic acid; 2-[4-oxo-5-carboxamido-9-(3-methylbenzyl)-9/-/-pyrido[3,4-ib]indolyl]acetic acid; 2-[4-oxo-5-carboxamido-9-(4-methylbenzyl)-9/-/-pyrido[3,4-ib]indolyl]acetic acid; 2-[4-oxo-5-carboxamido-9-(4-tertbutylbenzyl)-9/-/-pyrido[3,4-ib]indolyl]acetic acid; 2-[4-oxo-5-carboxamido-9-pentafluorobenzyl-9/-/-pyrido[3,4-ib]indolyl]acetic acid; 2-[4-oxo-5-carboxamido-9-(2-fluorobenzyl)-9/-/-pyrido[3,4-ib]indolyl]acetic acid; 2-[4-oxo-5-carboxamido-9-(3-fluorobenzyl)-9/-/-pyrido[3,4-ib]indolyl]acetic acid; 2-[4-oxo-5-carboxamido-9-(4-fluorobenzyl)-9/-/-pyrido[3,4-ib]indolyl]acetic acid; 2-[4-oxo-5-carboxamido-9-(2,6-difluorobenzyl)-9/-/-pyrido[3,4-ib]indolyl]acetic acid; 2-[4-oxo-5-carboxamido-9-(3,4-difluorobenzyl)-9/-/-pyrido[3,4-ib]indolyl]acetic acid; 2-[4-oxo-5-carboxamido-9-(2,5-difluorobenzyl)-9/-/-pyrido[3,4-jb]indolyl]acetic acid; 2-[4-oxo-5-carboxamido-9-(3,5-difluorobenzyl)-9/-/-pyπdo[3,4-ib]indolyl]acetic acid; 2-[4-oxo-5-carboxamido-9-(2,4-difluorobenzyl)-9/-/-pyrido[3,4-ib]indolyl]acetic acid; 2-[4-oxo-5-carboxamido-9-[2-(trifluoromethyl)benzyl]-9/-/-pyrido[3,4-ib]indolyl]acetic acid; 2-[4-oxo-5-carboxamido-9-[3-(trifluoromethyl)benzyl]-9/-/-pyrido[3,4-ib]indolyl]acetic acid; 2-[4-oxo-5-carboxamido-9-[4-(trifluoromethyl)benzyl]-9/-/-pyrido[3,4-ib]indolyl]acetic acid; 2-[4-oxo-5-carboxamido-9-[3,5-bis(trifluoromethyl)benzyl]-9/-/-pyrido[3,4-ib]indolyl]acetic acid; 2-[4-oxo-5-carboxamido-9-[2,4-bis(trifluoromethyl)benzyl]-9/-/-pyrido[3,4-ib]indolyl]acetic acid; 2-[4-oxo-5-carboxamido-9-(a-methylnaphthyl)-9/-/-pyrido[3,4-ib]indolyl]acetic acid; 2-[4-oxo-5-carboxamido-9-(b-methylnaphthyl)-9/-/-pyrido[3,4-ib]indolyl]acetic acid; 2-[4-oxo-5-carboxamido-9-(3,5-dimethylbenzyl)-9/-/-pyrido[3,4-ib]indolyl]acetic acid; 2-[4-oxo-5-carboxamido-9-(2,4-dimethylbenzyl)-9/-/-pyrido[3,4-ib]indolyl]acetic acid; 2-[4-oxo-5-carboxamido-9-(2-phenylbenzyl)-9/-/-pyrido[3,4-ib]indolyl]acetic acid; 2-[4-oxo-5-carboxamido-9-(3-phenylbenzyl)-9/-/-pyrido[3,4-ib]indolyl]acetic acid; 2-[4-oxo-5-carboxamido-9-(4-phenylbenzyl)-9/-/-pyrido[3,4-ib]indolyl]acetic acid; 2-[4-oxo-5-carboxamido-9-(1-fluorenylmethy)-9/-/-pyrido[3,4-ib]indolyl]acetic acid; 2-[4-oxo-5-carboxamido-9-(2-fluoro-3-methylbenzyl)-9/-/-pyrido[3,4-ib]indolyl]acetic acid; 2-[4-oxo-5-carboxamido-9-(3-benzoylbenzyl)-9/-/-pyrido[3,4-ib]indolyl]acetic acid; 2-[4-oxo-5-carboxamido-9-(2-phenoxybenzyl)-9/-/-pyrido[3,4-ib]indolyl]acetic acid; 2-[4-oxo-5-carboxamido-9-(3-phenoxybenzyl)-9/-/-pyrido[3,4-ib]indolyl]acetic acid; 2-[4-oxo-5-carboxamido-9-(4-phenoxybenzyl)-9/-/-pyrido[3,4-ib]indolyl]acetic acid; 2-[4-oxo-5-carboxannido-9-[3-[2-(fluorophenoxy)benzyl]]-9/-/-pyπdo[3,4-ib]indolyl]acetic acid; 2-[4-oxo-5-carboxamido-9-[3-[4-(fluorophenoxy)benzyl]]-9/-/-pyrido[3,4-ib]indolyl]acetic acid; 2-[4-oxo-5-carboxamido-9-[2-fluoro-3-(trifluoronnethyl)benzyl]-9/-/-pyπdo[3,4-£>]indolyl]acetic acid; 2-[4-oxo-5-carboxamido-9-[2-fluoro-4-(trifluoronnethyl)benzyl]-9/-/-pyrido[3,4-ib]indolyl]acetic acid; 2-[4-oxo-5-carboxamido-9-[2-fluoro-5-(trifluoromethyl)benzyl]-9H-pyrido[3,4-tb]indolyl]acetic acid; 2-[4-oxo-5-carboxamido-9-[3-fluoro-5-(trifluoromethyl)benzyl]-9/-/-pyrido[3,4-ib]indolyl]acetic acid; 2-[4-oxo-5-carboxamido-9-[4-fluoro-2-(trifluoronnethyl)benzyl]-9/-/-pyrido[3,4-ib]indolyl]acetic acid; 2-[4-oxo-5-carboxamido-9-[4-fluoro-3-(trifluoronnethyl)benzyl]-9/-/-pyrido[3,4-ib]indolyl]acetic acid; 2-[4-oxo-5-carboxamido-9-[2-fluoro-6-(trifluoronnethyl)benzyl]-9/-/-pyrido[3,4-tb]indolyl]acetic acid; 2-[4-oxo-5-carboxamido-9-(2,3,6-trifluorobenzyl)-9/-/-pyrido[3,4-ib]indolyl]acetic acid; 2-[4-oxo-5-carboxamido-9-(2,3,5-trifluorobenzyl)-9/-/-pyrido[3,4-tb]indolyl]acetic acid; 2-[4-oxo-5-carboxamido-9-(2,4,5-trifluorobenzyl)-9/-/-pyrido[3,4-ib]indolyl]acetic acid; 2-[4-oxo-5-carboxamido-9-(2,4,6-trifluorobenzyl)-9/-/-pyrido[3,4-tb]indolyl]acetic acid; 2-[4-oxo-5-carboxamido-9-(2,3,4-trifluorobenzyl)-9/-/-pyrido[3,4-ib]indolyl]acetic acid; 2-[4-oxo-5-carboxamido-9-(3,4,5-trifluorobenzyl)-9/-/-pyrido[3,4-tb]indolyl]acetic acid; 2-[4-oxo-5-carboxamido-9-[3-(trifluoronnethoxyl)benzyl]-9/-/-pyrido[3,4-ib]indolyl]acetic acid; 2-[4-oxo-5-carboxamido-9-[4-(trifluoronnethoxyl)benzyl]-9/-/-pyrido[3,4-ib]indolyl]acetic acid; 2-[4-oxo-5-carboxamido-9-[4-methoxy(tetrafluoro)benzyl]-9/-/-pyrido[3,4-ib]indolyl]acetic acid; 2-[4-oxo-5-carboxamido-9-(2-nnethoxybenzyl)-9/-/-pyrido[3,4-ib]indolyl]acetic acid; 2-[4-oxo-5-carboxamido-9-(3-nnethoxybenzyl)-9/-/-pyrido[3,4-ib]indolyl]acetic acid; 2-[4-oxo-5-carboxamido-9-(4-nnethoxybenzyl)-9/-/-pyrido[3,4-ib]indolyl]acetic acid; 2-[4-oxo-5-carboxannido-9-(4-ethylbenzyl)-9/-/-pyπdo[3,4-ib]indolyl]acetic acid; 2-[4-oxo-5-carboxamido-9-(4-isopropylbenzyl)-9/-/-pyrido[3,4-ib]indolyl]acetic acid; 2-[4-oxo-5-carboxamido-9-(3,4,5-trinnethoxybenzyl)-9/-/-pyrido[3,4-ib]indolyl]acetic acid; 2-[4-oxo-5-carboxamido-9-(3,4-nnethylenedioxybenzyl)-9/-/-pyrido[3,4-ib]indolyl]acetic acid; 2-[4-oxo-5-carboxamido-9-(4-nnethoxy-3-nnethylbenzyl)-9/-/-pyπdo[3,4-ib]indolyl]acetic acid; 2-[4-oxo-5-carboxamido-9-(3,5-dinnethoxybenzyl)-9/-/-pyπdo[3,4-ib]indolyl]acetic acid; 2-[4-oxo-5-carboxamido-9-(2,5-dinnethoxybenzyl)-9/-/-pyπdo[3,4-ib]indolyl]acetic acid; 2-[4-oxo-5-carboxamido-9-(4-ethoxybenzyl)-9/-/-pyrido[3,4-ib]indolyl]acetic acid; 2-[4-oxo-5-carboxamido-9-(cyclohexylnnethyl)-9/-/-pyrido[3,4-ib]indolyl]acetic acid; 2-[4-oxo-5-carboxamido-9-(cyclopentylnnethyl)-9/-/-pyrido[3,4-ib]indolyl]acetic acid; 2-[4-oxo-5-carboxamido-9-ethyl-9/-/-pyrido[3,4-ib]indolyl]acetic acid; 2-[4-oxo-5-carboxamido-9-(1-propyl)-9/-/-pyrido[3,4-ib]indolyl]acetic acid; 2-[4-oxo-5-carboxamido-9-(2-propyl)-9/-/-pyrido[3,4-ib]indolyl]acetic acid; 2-[4-oxo-5-carboxamido-9-(1-butyl)-9H-pyrido[3,4-]indolyl]acetic acid; 2-[4-oxo-5-carboxamido-9-(2-butyl)-9/-/-pyrido[3,4-ib]indolyl]acetic acid; 2-[4-oxo-5-carboxamido-9-isobutyl-9/-/-pyrido[3,4-ib]indolyl]acetic acid; 2-[4-oxo-5-carboxamido-9-[2-(1-phenylethyl)]-9/-/-pyrido[3,4-ib]indolyl]acetic acid; 2-[4-oxo-5-carboxamido-9-[3-(1-phenylpropyl)]-9/-/-pyrido[3,4-ib]indolyl]acetic acid; 2-[4-oxo-5-carboxamido-9-[4-(1-phenylbutyl)]-9/-/-pyrido[3,4-ib]indolyl]acetic acid; 2-[4-oxo-5-carboxamido-9-(1-pentyl)-9/-/-pyrido[3,4-tb]indolyl]acetic acid; 2-[4-oxo-5-carboxamido-9-(1-hexyl)-9/-/-pyrido[3,4-ib]indolyl]acetic acid; 4-[(9-benzyl-4-carbamoyl-1,2,3,4-tetrahydrocarbazol-6-yl)oxy]butyric acid; 3-[(9-benzyl-4-carbamoyl-1,2,3,4-tetrahydrocarbazol-θ-yOoxylpropylphosphonic acid; 2-[(9-benzyl-4-carbamoyl-1,2,3,4-tetrahydrocarbazol-6-yl)oxy]methylbenzoic acid; 3-[(9-benzyl-4-carbamoyl-7-n-octyl-1,2,3,4-tetrahydrocarbazol-6-yl)oxy]propylphosphonic acid; 4-[(9-benzyl-4-carbamoyl-7-ethyl-1,2,3,4-tetrahydrocarbazol-6-yl)oxy]butyric acid; 3-[(9-benzyl-4-carbamoyl-7-ethyl-1,2,3,4-tetrahydrocarbazol-6-yl)oxy]propylphosphonic acid; 3-[(9-benzyl-4-carbamoyl-7-ethyl-1,2,3,4-tetrahydrocarbazol-6-yl)oxy]propylphosphonic acid; (S)-(+)-4-[(9-benzyl-4-carbamoyl-7-ethyl-1,2,3,4-tetrahydrocarbazol-6-yl)oxy]butyric acid; 4-[9-benzyl-4-carbamoyl-6-(2-cyanoethyl)-1,2,3,4-tetrahydrocarbazol-6-yl]oxybutyric acid; 4-[9-benzyl-4-carboxamido-7-(2-phenylethyl)-1,2,3,4-tetrahydrocarbazol-6-yl]oxybutyric acid; 4-[9-benzyl-4-carboxamido-carbazol-6-yl]oxybutyric acid; methyl 2-[(9-benzyl-4-carbamoyl-1,2,3,4-tetrahydrocarbazol-6-yl)oxy]methylbenzoate; 4-[9-benzyl-4-carbamoyl-7-(2-cyanoethyl)-1,2,3,4-tetrahydrocarbazol-6-yl]oxybutyric acid; 9-benzyl-7-methoxy-5-cyanomethyloxy-tetrahydrocarbazole-carboxamide; [9-benzyl-4-carbamoyl-8-methyl-carbazole-5-yl]oxyacetic acid; and [θ-benzyM-carbamoyl-carbazole-δ-yl]oxyacetic acid, or pharmaceutically acceptable salts, solvates, prodrug derivatives, racemates, tautomers, or optical isomers thereof.

PLA2 inhibitors also include leukotriene synthesis inhibitors selected from the group consisting of methyl arachidonyl fluorophosphonate (MAFP), pyrroxyphene, ONO-RS-082, 1-[3-(4-octylphenoxy)-2-oxopropyl]indole-5-carboxylic acid, 1-[3-(4-octylphenoxy)-2-oxopropyl]indole-6-carboxylic acid, arachidonyl trifluoromethyl ketone, D609, 4-{3-[5-chloro-2-(2-{([(3,4-dichlorobenzyl)sulfonyl] amino}ethyl)-1-(diphe-nylmethyl)-1H-indol-3-yl] propyl}benzoic acid (WAY-196025), efipladib, 4-{2-[5-chloro-2-(2-{[(3,4-dichlorobenzyl)sulfonyl]amino}-ethyl)-1-(diphe-nylmethyl)-1H-indol-3-yl]ethoxy}benzoic acid, Ecopladib, (E)-N-[(2S,4R)-4-[N-(biphenyl-2-ylmethyl)-N-2-methylpropylamino]-1-[2-(2,-4-difluorobenzoyl)benzoyl] pyrrolidin-2-yl]methyl-3-[4-(2,4-dioxothiazolidi-n-5-ylidenemethyl) phenyl]acrylamide (RSC-3388), berberine, glutamine, Indoxam, Me-Indoxam or a pharmaceutically acceptable salt thereof.

Certain embodiments of the invention involve the administration of varespladib, methylvarespladib, LY43371 or a combination thereof and optionally at least one additional PLA2 inhibitor. The one additional PLA2 inhibitor may be selected from the group consisting of Compound 4, AZD2716, varespladib (LY 315920), methylated varespladib (LY333013), AIPLAI (Azadirachta indica PLA2 inhibitor), BMS-181162, LY311727, ARL-67974, FPL67047, SB-203347, Ro-23-9358, YM-26734, YM 26567, IS-741, MJ33, flunixin, Effipladib, Way 196025, Ecopladib, Giripladib, Variabilin, Indoxam, Me-Indoxam, SB 203347, PAF-AH, Darapladib, phosphatidylethanolamine (PE), phosphatidylserine (PS), phosphatidylcholine (PC), phosphatidylinositol (PI), and phosphatidylglycerol (PG) and mixtures thereof linked (conjugated) to at least one compound selected from the group consisting of carboxymethylcellulose (CMPE, CMC-Peor CME), hyaluronic acid (HYPE, HyPE, and Hyal-PE), heparin (HEPPE, HepPE, HePPE, Hepa-PE), chondroitine sulfate A (CSAPE, CsaPE, CsAPE), Polygeline (haemaccel) (HemPE, HEMPE), hydroxyethylstarch (HesPE, HESPE)(preferably Hyaluronic acid-linked phosphatidyl ethanolamine (HyPE)) and analogs, derivatives, pharmaceutically acceptable salts, enantiomers, diastereomers, solvates, polymorphs and mixtures thereof.

PLA2 inhibitors also include compositions comprising at least one phopholipid selected from the group consisting of phosphatidylethanolamine (PE), phosphatidylserine (PS), phosphatidylcholine (PC), phosphatidylinositol (PI), and phosphatidylglycerol (PG) and mixtures thereof linked (conjugated) to at least one compound selected from the group consisting of carboxymethylcellulose (CMPE, CMC-Peor CME), hyaluronic acid (HYPE, HyPE, and Hyal-PE), heparin (HEPPE, HepPE, HePPE, Hepa-PE), chondroitine sulfate A (CSAPE, CsaPE, CsAPE), Polygeline (haemaccel) (HemPE, HEMPE), hydroxyethylstarch (HesPE, HESPE) and mixtures thereof. Hyaluronic acid-linked phosphatidyl ethanolamine (HyPE) is an additional PLA2 inhibitor. These PLA2 inhibitors are further discussed in PCT publication WO2016081826A2, incorporated herein by reference.

Statins

Statins are HMG-CoA reductase inhibitors and are commonly-used to reduce high cholesterol levels associated with low-density lipoproteins (LDL). As used herein, "statins" are agents which act to inhibit 3-hydroxy-3-methylglutaryl-coenzyme A (HMG-CoA) reductase. Statins include but are not limited to atorvastatin, cerivastatin, fluvastatin, lovastatin, mevastatin, a monacolin (e.g., monacolin M, monacolin J, monacolin N, monacolin L, monacolin X, etc.), pitavastatin (also known as itavastatin), pravastatin, rosuvastatin, and simvastatin. See e.g. Oliveira E F, et al., *Expert Opin Ther Pat.* 2016; 26(11):1257-1272. In some embodiments, a combination of any two or more statins can be used. Importantly, soluble statin formulations (e.g. In Sol® simvistatin) that can be administered in an IV have not been previously tested in combination with sPLA2 inhibitors.

In some embodiments, the treatment according to the present invention comprises at least one PLA2 inhibitor, preferably varespladib and/or methylvarespladib, LY433771, Compound 4, or AZD2716, alone or in combination with one or more statin presented herein.

Statins for use herein include Atorvastatin, the chemical structure of which is presented below:

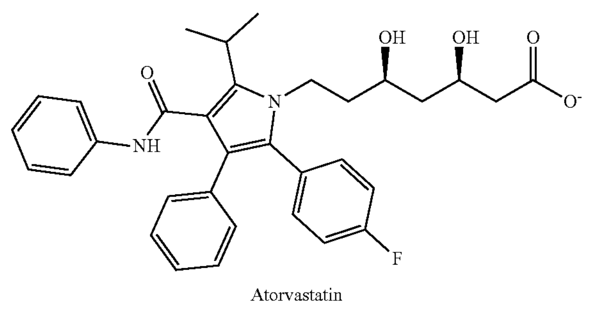 [SMILES: CC(C)c1c(C(=O)Nc2ccccc2)c(-c2ccccc2)c(-c2ccc(F)cc2)n1CC[C@@H](O)C[C@@H](O)CC(=O)[O-]]

Atorvastatin

Statins for use herein include Cerivastatin, the chemical structure of which is presented below:

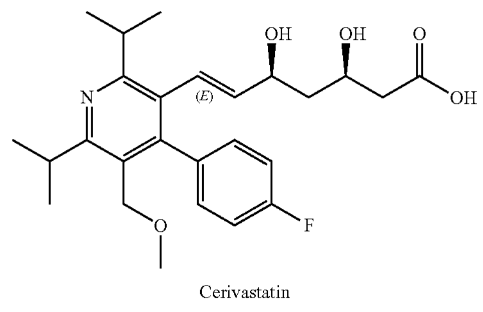 [SMILES: COCc1c(C(C)C)nc(C(C)C)c(/C=C/[C@@H](O)C[C@@H](O)CC(=O)O)c1-c1ccc(F)cc1]

Cerivastatin

Statins for use herein include Fluvastatin, the chemical structure of which is presented below:

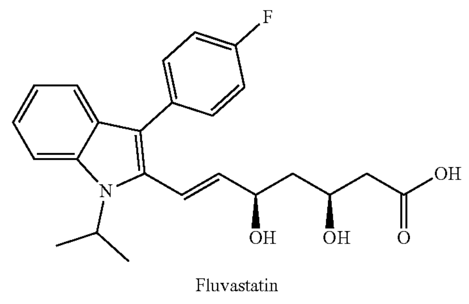 [SMILES: CC(C)n1c(/C=C/[C@H](O)C[C@H](O)CC(=O)O)c(-c2ccc(F)cc2)c2ccccc21]

Fluvastatin

Statins for use herein include Lovastatin, the chemical structure of which is presented below:

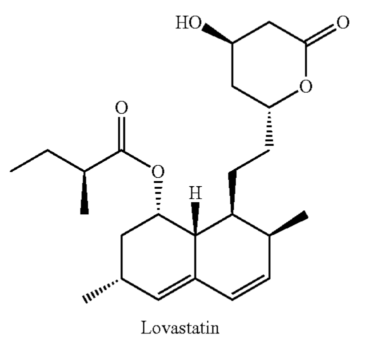 [SMILES: CC[C@H](C)C(=O)O[C@H]1C[C@@H](C)C=C2C=C[C@H](C)[C@H](CC[C@@H]3C[C@@H](O)CC(=O)O3)[C@H]21]
Lovastatin

Statins for use herein include Monacolins, including monacolin J, the chemical structure of which is presented below:

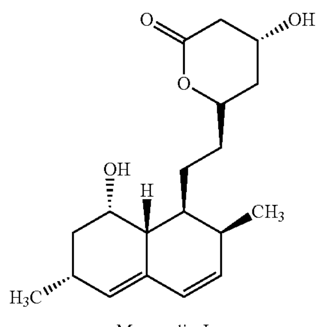
Monacolin J

Statins for use herein include Mevastatin, the chemical structure of which is presented below:

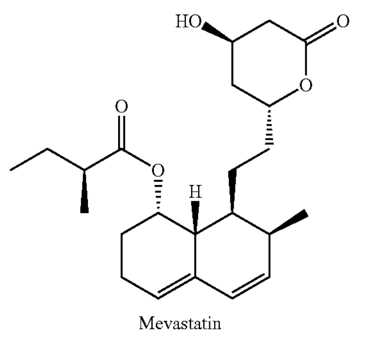 [SMILES: CC[C@H](C)C(=O)O[C@H]1CCC=C2C=C[C@H](C)[C@H](CC[C@@H]3C[C@@H](O)CC(=O)O3)[C@H]21]
Mevastatin

Statins for use herein include Pitavastatin, the chemical structure of which is presented below:

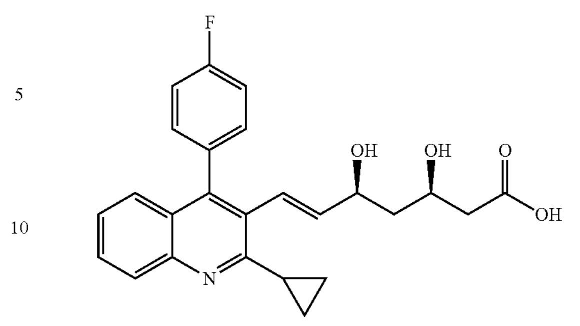
Pitavastatin

Statins for use herein include Pravastatin the chemical structure of which is presented below:

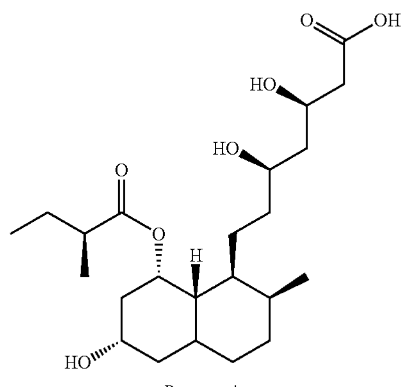
Pravastatin

Statins for use herein include Rosuvastatin, the chemical structure of which is presented below:

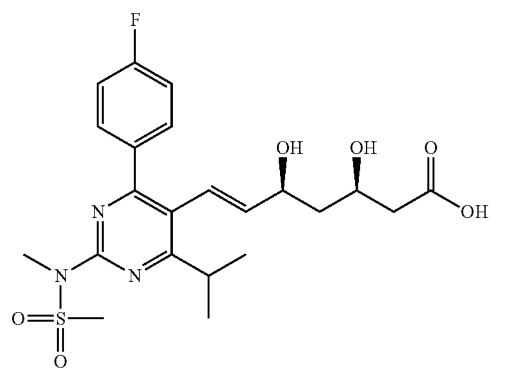
Rosuvastatin

Statins for use herein include Simvastatin, the chemical structure of which is presented below:

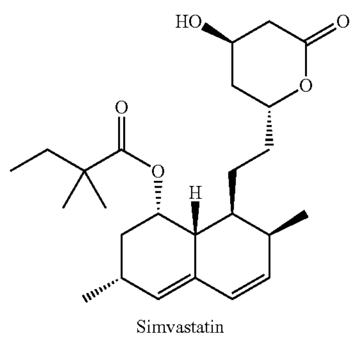 [SMILES: CCC(C)(C)C(=O)O[C@H]1C[C@@H](C)C=C2C=C[C@H](C)[C@H](CC[C@@H]3C[C@@H](O)CC(=O)O3)[C@H]21]

Simvastatin

Additional Agents

In some embodiments, the PLA2 inhibitor may be used as a combination therapy and administered in combination with one or more agents. In some embodiments, combination therapy may comprise administration of two or more active agents that are co-formulated (e.g., mixed together or combined in a single unit dosage form) or co-administered (both administered as part of a course of therapy to treat envenomation).

Pharmaceutical compositions and methods according to the present invention may further include epinephrine, diphenhydramine, a steroid, or a combination thereof. In one aspect, a PLA2 inhibitor may be used in combination with epinephrine. In another aspect, a PLA2 inhibitor may be used in combination with diphenhydramine. In another aspect, a PLA2 inhibitor may be used in combination with a steroid.

Pharmaceutical compositions and methods according to the present invention may include a small molecule with inhibitor activity against metalloproteinases. Useful metalloproteinase inhibitors, including but not limited to prinomastat and vorinostat, are further discussed in PCT publication WO2016081826A2.

Pharmaceutical compositions and methods according to the present invention may include a small molecule with inhibitor activity against serine proteases. Useful serine proteases inhibitors are further discussed in PCT publication WO2016081826A2.

Pharmaceutical compositions and methods according to the present invention may include anti-venom or with a whole or fragmented IgG from animal or recombinant source used to neutralize, specifically venom α-toxins and/or serine proteases. The general use of small molecule inhibitors with anti-venom is further discussed in PCT publication WO2016081826A2. Useful anti-venom compounds are further discussed in PCT publication WO2016081826A2.

Pharmaceutical compositions and methods according to the present invention may include other therapeutic agents, including antinausea agents, antibiotics, or inhibitors, including antibody-based inhibitors of enzymatic and non-enzymatic components present in venom. These additional therapeutic agents are further discussed in PCT publication WO2016081826A2.

Pharmaceutical compositions and methods according to the present invention may include lidocaine and/or bupivacaine as agents to assist in the local distribution of the active agents for further therapeutic benefit and analgesia while slowing the spread of venom by relaxation of lymphatic smooth muscle. Significantly, unlike anti-venom, compositions of the present invention may diffuse or penetrate nervous system tissues, blood clots and/or dead tissue found at envenomation sites, thus providing effective therapy where anti-venom exhibits reduced or negligible impact. The inclusion of lidocaine and/or bupivacaine may assist in having the agent, once administered more quickly reach its site of activity while potentially providing pain relief from the bite and prevention of pain from delivery of the drugs when any parenteral mechanism is used and for general analgesia.

Pharmaceutical compositions and methods according to the present invention may include a topical anesthetic. In the context of bites and stings, a topical anesthetic is a local anesthetic that is used to numb the surface of a body part and paralyze lymphatic smooth muscle, slowing the spread of venom. Topical anesthetics are available in creams, ointments, aerosols, sprays, lotions, and jellies. Examples include benzocaine, butamben, dibucaine, lidocaine, oxybuprocaine, pramoxine, proparacaine, proxymetacaine, and tetracaine (also named amethocaine). Efficacy of EMLA cream (eutectic mixture of local anesthetics) with that of LET solution (lidocaine, epinephrine, tetracaine) for local application with occlusive dressings or as solutions rubbed in are anticipated to slow the spread of venom.

Pharmaceutical compositions and methods according to the present invention may include spreading factor inhibitors. Spreading factor inhibitors may be chemical or physical and are further discussed in PCT publication WO2016081826A2.

Formulations

Pharmaceutical compositions and methods according to the present invention may include a composition comprising an effective amount of one or more PLA2 inhibitor(s) in combination with a sugar. Exemplary sugars include mannitol, sorbitol, erythritol, or mixtures thereof. The inclusion of mannitol and/or other sugars such as sorbitol and or erythritol may facilitate dissolution of the varespladib and/or a derivative thereof, to facilitate administration of the compound. The inclusion of mannitol and/or other sugars may add to the neuroprotective, hematoprotective and nephroprotective properties of varespladib by decreasing swelling and increasing urine output as well as alkalinizing (especially with the addition of bicarbonate diluent) the urine to clear hemoglobin and prevent pigment nephropathies. The inclusion of mannitol and/or other sugars may add to the protection from hemolysis. Examples of orally useful compositions includes ethanol and Polyethylene glycol (PEG) to improve the dispersion and maintain homogeneity in oral preparations of prodrug (e.g. methyl-varespladib) and drug (e.g. LY433771, Compound 4 or AZD2716) in animals and humans.

Pharmaceutical compositions and methods according to the present invention may include a composition comprising an effective amount of one or more PLA2 inhibitor(s) in combination with mannitol and/or hypertonic saline.

Pharmaceutical compositions and methods according to the present invention may include a composition comprising an effective amount of one or more PLA2 inhibitor(s) in combination with one or more carbon monoxide releasing compounds (e.g. $[Ru(CO)_3Cl_2]_2$ Molecular Weight: 512.01 CAS Number: 22594-69-0). In another aspect, a PLA2 inhibitor may be used in combination with a carbon monoxide releasing compound and poloxomers. In another aspect, a PLA2 inhibitor may be used in combination with a carbon monoxide releasing compound, poloxomers and MP, SP and/or other venom components from reptiles, arthropods and marine organisms vertebrate and invertebrate. The inclusion of such compounds may be useful in the clinical treatment of traumatic brain injury and/or blunt trauma.

Methods of Treatment

It has been discovered that 1H-indole-3-glyoxylamides such as varespladib and/or methylvarespladib or a carbazole compound such as LY433771 and other compounds such as LY311727, indoxam, methyl-indoxam, Compound 4, and AZD2716 are potent secreted phospholipase A2 (PLA2) inhibitors with excellent preclinical pharmacokinetic properties in treatment of stings from swarming hymenoptera including bees and wasps, clear in vivo efficacy, including via oral route of administration, and minimal safety risk to be used alone or in combinations with for the treatment of swarming hymenoptera envenomation and important medical conditions causing hemolysis and brain edema such as malaria, rickettsiosis, neurotuberculosis and traumatic brain injury.

The unexpected inhibition of a variety of venom components by PLA2 inhibitors suggests a direct regulatory role for PLA2 in the activity of many enzymatic and non-enzymatic venom components, and also a role in host-mediated responses that facilitate entry of non-enzymatic, tissue destroying toxins into host cells. Furthermore, specific PLA2 inhibitors exhibit anti-inflammatory activity, decreasing vascular permeability and decreasing the ability of venom to spread while small molecule therapeutics can diffuse to the site of venom deposition. This surprising combination of salutary effects (direct inhibition of the venom by PLA2 inhibitors and indirect effects) make PLA2 inhibitors an ideal multifunctional antidote to invertebrate (e.g. swarming hymenoptera) envenomation and other Type 11 sPLA2 mediated reactions, used as a therapy alone or in combination with other therapeutics.

Furthermore, PLA2 inhibitors are herein shown to have general anti-hemolytic properties alone or in conjunction with statins. This unexpected result suggests that there is a general therapeutic potential for PLA2 inhibitors alone or in combination with statins to treat hemolytic anemias, including paroxysmal nocturnal hemoglobinuria (PNH) or other diseases or conditions associated with osmotic fragility, including but not limited to myelinolysis, autoimmune spherocytosis, hereditary spherocytosis poisoning, severe burns, thalassemia, immunohemolytic anemia, and malaria. This treatment can further improve the stability of blood storage and reduce the need or substitute for cyclosporine in the setting of angioedema and rheumatoid arthritis.

In one embodiment, the present invention relates to a method for the use of at least one PLA2 inhibitor, alone or in combination with at least one additional agent, by one or more routes of administration for the treatment of envenomation (e.g., a venomous hymenoptera bite or sting such as from bees, wasps, scorpion, spider, cnidarian or other swarming hymenoptera bite or sting as otherwise defined herein).

In another embodiment, the present invention relates to a method for the use of at least one PLA2 inhibitor, alone or in combination with at least one additional agent, by one or more routes of administration for the treatment of cerebral malaria.

In another embodiment, the present invention relates to a method for the use of at least one PLA2 inhibitor, alone or in combination with at least one additional agent, by one or more routes of administration for the treatment of brain swelling associated with head trauma or traumatic brain injury.

In another embodiment, the present invention relates to a method for the use of at least one PLA2 inhibitor, alone or in combination with at least one additional agent, by one or more routes of administration for the treatment of traumatic conditions such as traumatic brain injury (e.g. such as in combat) and blunt trauma with and without incipient or actual hematopathology, kidney injury (including kidney failure) or brain injury or combinations of these complex conditions (in the absence of envenomation).

In another embodiment, the present invention relates to a method for the use of at least one PLA2 inhibitor, alone or in combination with at least one additional agent, by one or more routes of administration for the treatment of envenomation, especially in envenomation cases at risk for or in combination with incipient or actual hematopathology, brain injury (e.g. bleeding, swelling) and or kidney failure.

In another embodiment, the present invention relates to a method for the use of at least one PLA2 inhibitor, alone or in combination with at least one additional agent, for the treatment of general hemolysis prevention in the setting of infectious disease (e.g. hemolytic *streptococcus*), metabolic and genetic disorders (e.g. G6PD deficiency, sickle cell disease), hemolytic uremic syndrome, and/or other hemolytic toxins and processes of internal or external origin and processes.

In one aspect, provided is a method of treating envenomation wherein a patient is treated with a therapeutically effective amount of at least one PLA2 inhibitor within a time interval initiating from suspected or confirmed envenomation, objective or clinical suspicion of elevated sPLA2 levels or other indicators of envenomation by field, pre-hospital, laboratory, bedside or clinical testing. In some instances, the treatment is provided to mitigate or reduce the need for traditional anti-venom and/or to reduce the cost and requirement for hospital, especially, clinically intensive resources such as intensive care (ICU time).

The methods disclosed herein have several applications in medicine.

The methods disclosed herein are directed to a method of reducing the likelihood of death or injury from envenomation in a mammal including a human, the method comprising initiating administration to a patient suspected of having or known to have suffered envenomation, the method comprising administering an effective amount of a PLA2 inhibitor or a combination of compounds (which may include a PLA2 inhibitor) administered together or separately after envenomation or the event triggering brain swelling, but prior to the occurrence of injury, especially substantial injury, caused by local, regional or systemic envenomation.

The methods disclosed herein are directed to a method of reducing the likelihood of death or injury in a patient suspected of having or known to have suffered another trigger of brain swelling (by envenomation or another cause), the method comprising administering an effective amount of a PLA2 inhibitor or a combination of compounds (which may include a PLA2 inhibitor) administered together or separately after the event triggering brain swelling, but prior to the occurrence of injury, especially substantial injury, caused by local, regional or systemic envenomation.

The methods disclosed herein comprise treating a subject who suffers from Large Local Reactions (LRR) resulting from envenomation from a swarming hymenoptera and by administering to the subject a composition comprising a therapeutically effective amount of at least one PLA2 inhibitor with or without a therapeutically effective amount of at least one statin, optionally with other agents described herein.

In some embodiments, the methods disclosed herein comprise treating a subject who suffers from hemolysis resulting from infection by a tropical disease (including but not limited to dengue hemorrhagic fevers, Ebola), by administering to the subject a composition comprising a therapeutically effective amount of at least one PLA2 inhibitor with a therapeutically effective amount of at least one statin, optionally with other agents described herein.

In some embodiments, the methods disclosed herein comprise treating a subject who suffers from hemolysis resulting from angioedema or paroxysmal nocturnal hemoglobinuria by administering to the subject a composition comprising a therapeutically effective amount of at least one PLA2 inhibitor with or without a therapeutically effective amount of at least one statin, optionally with other agents described herein.

In some embodiments, the methods disclosed herein comprise treating a subject who suffers from cerebral edema from infections, venomous, traumatic or osmotic causes by administering to the subject a composition comprising a therapeutically effective amount of at least one PLA2 inhibitor with or without a therapeutically effective amount of at least one statin, optionally with other agents described herein.

In some embodiments, the methods disclosed herein comprise treating a subject who suffers from a venom-induced cardiomyopathy by administering to the subject a composition comprising a therapeutically effective amount of at least one PLA2 inhibitor with or without a therapeutically effective amount of at least one statin, optionally with other agents described herein.

In some embodiments, the methods disclosed herein comprise treating a subject who requires acute neuroprotection, resulting from axotomy, demyelination, pathological neurolysis or ischemic stroke, by administering to the subject a composition comprising a therapeutically effective amount of at least one PLA2 inhibitor with or without a therapeutically effective amount of at least one statin, optionally with other agents described herein.

In some embodiments, the methods disclosed herein comprise treating a subject who suffers from venom, hemoglobin, or myoglobin-induced kidney failure, by administering to the subject a composition comprising a therapeutically effective amount of at least one PLA2 inhibitor with or without a therapeutically effective amount of at least one statin, optionally with other agents described herein.

The methods described herein may further relate to a method of treating a patient with multiple sclerosis and/or other acute demylenation syndromes resulting from snake envenomation. The methods disclosed herein further relate to a method of treating a patient with a mast cell disease (e.g. mastocytosis), anaphylactic reaction (IgE mediated), anaphylactoid reaction (non-IgE-mediated), or angioedema with complement-mediated pathway wherein treatment of a patient with a therapeutically effective amount of a composition according to the present invention, comprising administering at least one PLA2 inhibitor (e.g. sPLA2 inhibitor) optionally in combination with a statin, to the patient within a time interval initiating from suspected or confirmed event triggering the mast cell disease or other reaction, objective or clinical suspicion of elevated sPLA2 levels or other indicators of symptoms. In some embodiments, this treatment will mitigate or reduce the need for traditional methods of treatment, such as cyclosporine and omalizumab, and/or to reduce the cost and requirement for hospital, especially, clinically intensive resources such as intensive care (ICU time).

Subject

In some embodiments, the subject is at risk for or suffering from a wasp or bee envenomation or other pathological conditions causing hemolysis, cerebral edema, acute kidney injury and non-anaphylactic shock such as hymenoptera. In other embodiments, the subject is at risk of envenomation from swarming hymenoptera, from trauma, cerebral malaria and/or mast-cell diseases, and may be at risk of hemotoxic, neurotoxic, cytotoxic, cardiotoxic or myotoxic tissue damage, limb or ocular injury with or without resulting kidney failure, multiple organ failure and/or cardiovascular collapse due to envenomation by a parasitic lifeform (e.g. malaria, *Rickettsia* or *Babesia*). In other embodiments, the subject is at risk for or suffering from envenomation in combination with incipient or actual hematopathology, brain injury (e.g. bleeding, swelling) and/or kidney failure.

In some embodiments, the subject has been envenomated with a dose of venom (e.g., hymenoptera venom) that is higher than the average $LD_{50}$ for the venom in a human or non-human vertebrate. In some embodiments, the subject has been envenomated with a dose of venom that is lower than the average $LD_{50}$ for the venom in a human or non-human vertebrate. In some embodiments, the subject has been envenomated with a dose of venom that is at least 0.5 times the average $LD_{50}$ for the venom in a human or non-human vertebrate. In some embodiments the subject has been envenomated with a dose of venom that is at least 2-times the average $LD_{50}$ for the venom in a human or non-human vertebrate. The surprising finding of the in vivo efficacy of PLA2 inhibitors against bee venom may lead to the development of inhibitors for previously-uninhibited invertebrate Type 111 sPLA2 envenomations (e.g. spiders, scolopendra, marine organisms).

Administration Regimens

In some embodiments, the method of treatment be administered a number of hours after envenomation, for example, as a first line treatment for severe bee stings in a hospital or other patient care facility.

In the case of evenomation, the PLA2 inhibitor is preferably administered within a time interval initiating from suspected or confirmed envenomation or other event benefitting from the supression of PLA2 levels, objective or clinical suspicion of pathologically elevated sPLA2 levels or other indicators of envenomationsuch as cerebral edema or AKI, for example, by field, pre-hospital, laboratory, bedside or clinical testing, described herein within 0.1 (i.e., immediately or as soon as possible) to 24 hours after a bite or sting infection, or prior to a rise in sPLA2 levels, other correspondingly abnormal laboratory value which evidence that envenomation or brain swelling has occurred and/or clinical signs or symptoms suggestive of venom toxicity and/or brain swelling or as prophylaxis (e.g. occupational high-risk of exposure).

In some embodiments, the treatment regimen may stretch over a number of hours to a day to several weeks to months or years as determined by a competent caregiver (treating physician). Oral dosing and/or intravenous infusion may be preferred for patient convenience and tolerance. With oral dosing, one to four oral doses per day, each from about 0.01 to 100 mg/kg of body weight with exemplary doses from about 0.1 mg/kg to about 10 mg/kg.

In some embodiments, the PLA2 inhibitor may be used as a combination therapy. In some embodiments, combination therapy may comprise administration of 2 or more active agents that are co-formulated (e.g., mixed together or combined in a single unit dosage form) or co-administered (both administered as part of a course of therapy to treat envenomation). The co-administered agents can be administered simultaneously (e.g., as two or more separate unit dose forms, as simultaneous oral and IV administration, and the like) or can be administered at about the same time (concurrently) or sequentially (e.g., within about a minute or two of each other, about 10 min of each other, within about 30 min of each other, or within about 60 min of each other, or within 90 to 120 minutes of each other, or within 180 minutes of each other). Agents also may be administered at different times as part of the same course of therapy. For example, a patient may be administered one agent daily and a second agent weekly, as part of the same course of therapy. Similarly, a patient may receive an initial treatment (e.g., of varespladib and/or methylvarespladib) to initiate acute treatment of suspected or confirmed envenomation and a second treatment (e.g. anti-venom or specific anti-toxin IgG) subsequently (e.g., within 12 hours, within 24 hours, or within 36 hours, for example) as part of the same course of therapy. Additional exemplary combination therapies and co-formulations are detailed in PCT publication WO2016081826A2.

In one embodiment, the PLA2 inhibitor (e.g. varespladib, methylvarespladib, LY433771 or AZD2716) is administered to an envenomated subject without administration of an anti-venom, specific antibody or other small molecule MP inhibitor, or other small molecule SP inhibitor. In some approaches varespladib and/or methylvarespladib is administered to an envenomated subject and no administration of anti-venom, other small molecule MP inhibitor or other small molecule SP inhibitor occurs for a period after administration of the PLA2 inhibitor. That period of time may be at least about 1 hour, at least about 2 hours, at least about 3 hours at least about 4 hours at least about 5 hours at least about 10 hours at least about 12 hours or at least about 24 hours. In other embodiments the varespladib and/or methylvarespladib may be co-administered or co-formulated with a specific or polyvalent anti-venom mixture.

Route of Administration

The treatment may be administered by a variety of techniques, including but not limited to through use of a manual or auto-injecting device that may be needle-based and that may optionally include a jet-injector, an intranasal drug delivery device, a nebulizer, a metered dose inhaler or a spray device or an oral formulation such as pills, tablets, elixirs, or suppositories.

In some instances, the treatment may be initially administered by injection via needle or propulsion without a needle (e.g. jet injector or by aerosol administration) or orally, with further dosages of active ingredients being provided by any number of routes of administration in order to maintain effective concentrations of active in the patient until such time as therapeutic intervention is halted for whatever reason, including the decision to place the patient on more traditional anti-venom compositions because the level of the activity is increasing in the patient to the upper levels of its therapeutic index or because the patient condition has resolved or at least equilibrated making further administration unnecessary.

In some instances, the treatment may be administered in the form of injectable solutions (which may be preferred for initial treatment in combination with an auto or pen-injecting device), powders, liposomes, ointment, and/or aerosols and may include active ingredient(s) conjugated to another compound for specific targeting (e.g. nanoparticles or antibodies). Additional exemplary routes of administration are further detailed in PCT publication WO2016081826A2.

Dosage

Generally, dosages and routes of administration of the treatment described herein are determined according to the size and condition of the subject, according to standard pharmaceutical practices. Dose levels employed can vary widely, and can readily be determined by those of skill in the art. Typically, amounts in the milligram up to gram quantities are employed. The dosage administered may vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In general, the PLA2 inhibitor will be administered to a subject so that a therapeutically effective amount is received. A therapeutically effective amount may conventionally be determined for an individual patient by administering the active compound in increasing doses and observing the effect on the patient, for example, reduction in paralysis, tissue damage or suppression of increasing sPLA2 activity levels, or a reduction in other symptoms or signs associated with hymenoptera bite or sting or brain swelling.

Exemplary dosing ranges already tested in clinical trials for other indications are likely in therapeutic range for treatment of hymenoptera bites or stings or other indications described herein. See e.g. Dennis, E. A.; et al. Phospholipase A2 enzymes: Physical structure, biological function, disease implication, chemical inhibition, and therapeutic intervention. *Chem. Rev.* 2011, 111, 6130-6185, and Abraham, E. et al. Efficacy and safety of LY315920Na/S-5920, a selective inhibitor of 14-kDa group IIA secretory phospholipase A2, in patients with suspected sepsis and organ failure. *Crit. Care Med.* 2003, 31, 718-728, each incorporated herein by reference. These include 2.4-4.8 mg/kg/day.

In some embodiments, the active compounds may be administered in a manner and a dose to achieve in the animal a blood level concentration of sPLA2 or other inhibitor of from 0.01 to 15,000 ng/ml and preferably a concentration of 1 to 1000 ng/ml.

In some instances, the sPLA2 inhibitor has a lower $IC_{50}$ for human PLA2 compared to the $IC_{50}$ for venom PLA2. In some embodiments, the $IC_{50}$ for venom PLA2 is equivalent to, 10-fold, 100-fold, 1000-fold or lower than known for human PLA2.

In some instances, a daily dosage of active compound may be about 0.1 to 500 milligrams per kilogram of body weight. Ordinarily 0.5 to 50, and preferably 1 to 25 milligrams per kilogram per day given in divided doses 1 to 6 times a day or in sustained release form is effective to obtain desired results. Depending on the patient's state, a lower dose range or a higher dose range is given prior to the onset of symptoms or signs of bee sting inducing conditions (i.e., as determined clinically or potentially by increase in sPLA2 levels in a hospital setting), while a higher dose may be given when aggressive intervention is indicated to combat rising sPLA2 levels. In general, the PLA2 inhibitor will be administered to an animal so that a therapeutically effective amount is received. A therapeutically effective amount may conventionally be determined for an individual patient by administering the active compound in increasing doses and observing the effect on the patient, for example, reduction in paralysis, tissue damage or suppression of increasing sPLA2 activity levels, or a reduction in other symptoms or signs associated with bee sting. Generally, the compound should be administered in a manner and a dose to achieve in the animal a blood level concentration of sPLA2 or other inhibitor of from 0.01 to 15,000 ng/ml and preferably a concentration of 1 to 1000 ng/mL. The treatment regimen may stretch over a number of hours to a day to several weeks to months or years as determined by a competent caregiver (treating physician). Oral dosing and/or intravenous infusion may be preferred for patient convenience and tolerance. With oral dosing, one to four oral doses per day, each from about 0.01 to 100 mg/kg of body weight with exemplary doses from about 0.1 mg/kg to about 10 mg/kg.

Therapeutically effective doses for statins include those already tested in clinical trials for other indications. See e.g. Oliveira E F, et al., *Expert Opin Ther Pat.* 2016; 26(11): 1257-1272. Exemplary dosing ranges are likely in therapeutic range for treatment of hymenoptera bites or stings or other indications described herein. Statins may be administered at doses determined to be safe and effect for treatment of chronic lipidemia using oral dosage forms. In some embodiments, the active compounds may be administered in a manner and a dose to achieve in the animal a blood level concentration of statin from 0.01 to 15,000 ng/ml and preferably a concentration of 1 to 1000 ng/ml. Exemplary dosage ranges for statins further include amounts of statin sufficient, when dispersed, dissolved or diluted with a pharmaceutically-acceptable carrier (excipient) to yield statin concentrations of between about 0.000001, 0.00001, 0.0001, 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 725 to about 750 μM or as high as 800, 850, 900, 950 or 1,000 μM.

Because the indications for use according to the present invention (e.g., treatment of bee or snake envenomation or cerebral malaria) require immediate treatment, rather than oral administration and may be given as an IV or liquid formulation. In some instances, statins may be administered in liquid form, such as in a water soluble form. Exemplary dosage ranges for the statins sufficient, when dispersed, dissolved or diluted with a pharmaceutically-acceptable carrier (excipient) to yield statin concentrations of between about 500 nM and 10 μM.

Exemplary dosage ranges for the metalloproteinase inhibitor, PLA2 inhibitor and serine protease inhibitor include amounts of the inhibitors sufficient, when dispersed, dissolved or diluted with a pharmaceutically-acceptable carrier (excipient) to yield inhibitor concentrations of between about 0.000001, 0.00001, 0.0001, 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 725 to about 750 μM or as high as 800, 850, 900, 950 or 1,000 μM. These exemplary dosage ranges also apply to the adjuvant therapeutics described herein. Dosages of between about 0.000001, 0.00001, 0.0001, 0.001, 0.01, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 230, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 to about 500 μM are possible). Additional exemplary dosages are further detailed in PCT publication WO2016081826A2.

Formulations

Formulations comprising a PLA2 inhibitor (e.g., varespladib or methylvarespladib) and optionally other active compounds disclosed herein and one or more pharmaceutically acceptable excipients (e.g., saline) are provided. In one aspect, such formulations are at physiologically acceptable pH (e.g., about 7.4-8.5) e.g. when solubilized in 58% v/v 8.4% bicarbonate and 42% v/v 10% dextrose solution. Others include ratios of mannitol:citrate:drug of 1:1, 2:1, 3:1, 4:1, 5:1 with and without bicarbonate 4.2% or 8.4% with or without additional dextrose. In other aspects, such formulations include other sugars such as sorbitol, erythritol, or mixtures thereof with or without mannitol, at ratios of sugar:citrate:drug of 1:1, 2:1, 3:1, 4:1, and 5:1. Such formulations may enable more rapid dissolving of the drug or prodrug. Methylcellulose, polyethylene glycol (PEG), and nanoparticle delivery systems may be used to improve absorption of oral formulations. Such formulations may be amenable to storage and subsequent use with the drug, prodrug or combinations remaining intact for prolonged periods of time (e.g., during storage) and converted to varespladib with or without other components after administration to an individual (e.g., an adult, child, or infant). In some embodiments, the drug, prodrug or combinations are stored as a dry powder or powders (especially a lyophilized powder) and the formulation is generated by dissolving the dry powder in saline or other diluent prior to administration. In one aspect, formulations are provided, e.g., formulations comprising the drug, prodrug or combinations at molar equivalents of about any of 1 ng/ml to 1 μg/ml to 0.01, mg/ml, 0.1 mg/ml, 1 mg/ml, 5 mg/ml, 10 mg/ml, 25 mg/ml, 50 mg/ml, 75 mg/ml, 100 mg/mL, 125 mg/ml, 150 mg/mL, 175 mg/mL, or 200 mg/ml or 400 mg/ml or 600 mg/ml or 800 mg/mL or 1000 mg/mL of parent drug (e.g., varespladib), wherein the molar equivalent of drug, prodrug or combinations is the amount of drug, prodrug or combinations that would result in the indicated amount of parent drug upon complete conversion. For any amount (e.g., dosage) of drug, prodrug or combinations described herein, also contemplated is the molar equivalent of prodrug for that amount of parent drug. Single bolus formulations are also provided, e.g., up to about any of 5 ml, 10 ml, or 15 ml (at, for example, the stoichiometric prodrug equivalent of about 1450 mg to about 1600 mg of parent drug, such as varespladib) or in examples of pill, capsule or oral elixir forms: 1 mg to 100 mg, 250 mg, 500 mg, 1000 mg for oral dosing once, twice, three times per day to achieve serum concentrations of 10 μM, 100 μM, 1 nM, 10 nM, 50 nM, 100 nM, 200 nM, 500 nM, 1 uM, 10 uM, 100 uM and in non-human animals up to 1, 10, 25, 50, 100, 150 mg/kg/day but preferably 0.5 to 100 mg/kg/day in single or divided doses.

The PLA2 inhibitor may be used at a concentration, by weight, of 0.01 to 99.9 percent of the formulation, or in some cases a concentration, by weight, of 0.001 to 99.9 percent of the formulation. Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Exemplary Embodiments

Provided below are exemplary, non-limiting embodiments of the methods described in this disclosure.

Significantly, unlike anti-venom, exemplary compositions of the present invention can diffuse or penetrate nervous system tissues, blood clots and/or dead tissue found at envenomation sites, thus providing effective therapy where anti-venom exhibits reduced or negligible impact. The inclusion of lidocaine and/or bupivacaine may assist in having the agent, once administered more quickly reach its site of activity while potentially providing pain relief from the bite and prevention of pain from delivery of the drugs when any parenteral mechanism is used and for general analgesia.

In some embodiments, especially when one or more of the above-described compounds (preferably, small molecules) is combined with anti-venom or specific antibody or antibody fragment, these compositions may be administered a number of hours after envenomation, for example, as a first line treatment for snakebite or invertebrate bite or sting in a hospital or other patient care facility.

In one embodiment, the present invention relates to a method for the use of at least one PLA2 inhibitor, such as, 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, alone or in combination with at least one additional bioactive agent (including an additional PLA2 inhibitor preferably including varespladib, methylvarespladib or {9-[(phenyl)methyl]-5-carbamoylcarbazol-4-yl}oxyacetic acid (LY433771), by one or more routes of administration (in certain embodiments, AZD2716 is administered orally as are indoxam or methylindoxam) for the treatment of envenomation (e.g., a venomous snake or invertebrate such as hymenoptera bite or sting such as from bees, wasps, scorpion, spider, cnidarian or other swarming hymenoptera, as otherwise defined herein).

In one embodiment, the present invention relates to a method for the use of at least one PLA2 inhibitor, such as, 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, alone or in combination with at least one additional bioactive agent (including an additional PLA2 inhibitor preferably including varespladib, methylvarespladib or {9-[(phenyl)methyl]-5-carbamoylcarbazol-4-yl}oxyacetic acid (LY433771), by one or more routes of administration (in certain embodiments, AZD2716 is administered orally as are indoxam or methylindoxam) for the treatment of cerebral malaria.

In one embodiment, the present invention relates to a method for the use of at least one PLA2 inhibitor, such as, 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, alone or in combination with at least one additional bioactive agent (including an additional PLA2 inhibitor preferably including varespladib, methylvarespladib, or {9-[(phenyl)methyl]-5-carbamoylcarbazol-4-yl}oxyacetic acid (LY433771), by one or more routes of administration (in certain embodiments, AZD2716 is administered orally as are indoxam or methylindoxam) for the treatment of head trauma or traumatic brain injury.

In one embodiment, the present invention relates to a method for use of at least one PLA2 inhibitor, such as 3-(5'-Benzyl-2'-carbamoylbiphenyl-3-yl) propanoic acid (Compound 4) or AZD2716, or alternatively, LY433771, or its biologically active analogs, alone or in combination with one or more PLA2 inhibitor(s) (AZD2716 may be preferably administered with at least one additional PLA2 inhibitor, especially including varespladib, methyl varespladib and/or LY433771) and/or one or more additional bioactive agents useful in the present invention including inhibitors of metalloproteinases and/or serine proteases (SPs) and/or acetylcholinesterases and/or other venom components by one or more routes of administration (especially including orally for AZD2716) immediately or as soon as is possible after envenomation (often no more than 24 hours, even more often no more than 12 hours, preferably no more than about 6 hours, even more preferably no more than about 1 hour, even more often immediately after the realization that the patient has been subjected to envenomation) and for a period of time as long as it takes to have the patient taken to a hospital or other point of care facility for further diagnosis and/or treatment. Optionally, therapy is provided for a day to several weeks afterwards by one or more routes of delivery and formulation depending upon the setting and condition of the patient. In some instances, the method may be used for the treatment of envenomation (e.g., a venomous hymenoptera bite or sting such as from bees, wasps, scorpion, spider, cnidarian or other swarming hymenoptera bite or sting, as otherwise defined herein). In some instances, the method may be used for the treatment of cerebral malaria. In some instances, the method may be used for the treatment of head trauma or traumatic brain injury.

In one embodiment, the method utilizes an effective amount of PLA2 inhibitor (preferably, AZD2716 and/or LY43371 and optionally 1H-Indole-3-glyoxylamides, especially varespladib, methylvarespladib or mixtures thereof) as the sole agents to treat the subject suffering from an envenomation or other brain swelling.

In another embodiment, 1H-Indole-3-glyoxylamide, such as varespladib and/or methylvarespladib and/or optionally 3-(5'-Benzyl-2'-carbamoylbiphenyl-3-yl) propanoic acid (Compound 4), and/or AZD2716 and/or LY43371 and/or indoxam or methylindoxam and optionally camostat (N,N-dimethylcarbamoylmethyl,4-4-guanidinobenzoyloxy-phenylacetate or camostate) and/or gabexate (ethyl-p[6-guanidinohexanoyloxy]-benzoate methansulfonate), preferably at least varespladib, is co-administered with an acetylcholinesterase inhibitor (AChl) (e.g. neostigmine, edrophonium, or pyridostigmine, each preferably with atropine or glycopyrrolate) to provide a particularly effective universal antiparalytic whose significant anti-hemotoxic activity is conferred by varespladib and/or methylvarespladib, camostat and/or gabexate. In certain embodiments, the composition to be administered contains an effective amount of at least versapladib or methylvarespladib.

In some aspects, the invention utilizes an effective amount of a PLA2 inhibitor (preferably, 1H-Indole-3-glyoxylamide, such as varespladib and/or methylvarespladib and/or optionally 3-(5'-Benzyl-2'-carbamoylbiphenyl-3-yl) propanoic acid (Compound 4), and/or AZD2716 and/or LY43371 and/or indoxam or methylindoxam) as the sole agent or agents to treat the subject suffering from an envenomation or brain swelling. It has been discovered that both varespladib and methylvarespladib exhibit potent PLA2 inhibition as well as, at times, metalloproteinase and/or serine protease inhibition and may be used alone or in combination to great effect as optional agents in combination with AZD2716 and/or LY43371 to treat envenomation. In alternative embodiments, the invention may additionally comprise effective amounts of one or more additional agents including one or more additional PLA2 inhibitors and one or more metalloproteinase inhibitors (e.g. prinomastat, marimastat, vorinostat or batimastat) and when used topically one or more at least one spreading factor inhibitor (e.g. EMLA or LET).

In some aspects, the invention utilizes an effective amount of a PLA2 inhibitor (preferably, 1H-Indole-3-glyoxylamide, such as varespladib and/or methylvarespladib and/or 3-(5'-Benzyl-2'-carbamoylbiphenyl-3-yl) propanoic acid (Compound 4) and/or optionally AZD2716 and/or LY43371 and/or indoxam or methylindoxam) as the sole agent or agents to treat the subject suffering from an envenomation or brain swelling. In one embodiment, the invention may further comprise effective amounts of one or more agents including, for example, epinephrine or diphenhydramine.

In one aspect, the method of treatment uses at least one active component, in some instances at least two active components and in other instances no more than two active components including at least one PLA2 inhibitor (such as AZD2716 and/or LY43371), and optionally at least one additional agent selected from the group consisting of a selective PLA2 inhibitor (PLA2 inhibitor which also may function as an effective metalloproteinase inhibitor), a metalloproteinase inhibitor, a serine protease inhibitor, one or more acetylcholinesterase inhibitors, a NMDA receptor antagonist, an L-aminooxidase inhibitor, a hyaluronidase inhibitor and a spreading factor inhibitor to treat a subject who suffers from an envenomation. Initial administration may be at the time of envenomation and often within a period of several hours (1 minute to 12 hours) to less than about an hour after an envenomation, sometimes no more than about 1 to about 20 minutes, sometimes about 1 to about 10 minutes, after an envenomation by, for example, a bee sting. In other embodiments, especially when one or more of the above-described compounds (preferably, small molecules) is combined with anti-venom, these compositions may be administered a number of hours after envenomation before or after receiving anti-venom but preferably before, for example, as a first line treatment for bee stings in a hospital or other patient care facility. In some embodiment, or in addition, sequential dosing of PLA2s may be used. In some aspects, the invention utilizes an effective amount of AZD2716 and/or LY43371 as a PLA2 inhibitor (optionally, a 1H-Indole-3-glyoxylamide, such as varespladib and/or methylvarespladib and/or optionally AZD2716 and/or LY43371 and/or indoxam or methylindoxam) as the sole agent or agents to treat the subject suffering from an envenomation.

Treatment using 3-(5'-Benzyl-2'-carbamoylbiphenyl-3-yl) propanoic acid (Compound 4) and/or AZD2716, while exhibiting no notable inhibition against bee venom PLA2 inhibition or venoms containing little sPLA2 content (e.g. Boomslang), still result in survival and preservation of end-organ structure and function (e.g. renal as in Example 7). In alternative embodiments, the invention may additionally comprise effective amounts of one or more additional agents including one or more additional PLA2 inhibitors (as otherwise described herein, often indoxam or methy-indoxam) one or more metalloproteinase inhibitors (e.g. marimastat, prinomastat, tanomastat, vorinostat, batimastat, ilomastat and antibiotics such as doxycycline, cefixime and other cephalosporins), one or more serine protease inhibitors (e.g. nafamostat, which also has metalloproteinase inhibitory effects in some venoms, gabexate and camostat or camostate), at least one spreading factor inhibitor and at least one NMDA receptor antagonist, among others and including lidocaine and/or bupivacaine which may be included in effective amounts in order to increase blood flow in the area in which the composition is administered in order to increase biodistribution to the active site of the agent(s).

In another embodiment, 1H-Indole-3-glyoxylamide, such as varespladib and/or methylvarespladib and/or optionally AZD2716 and/or LY43371 and/or indoxam or methylindoxam, and/or 3-(5'-Benzyl-2'-carbamoylbiphenyl-3-yl) propanoic acid (Compound 4), with one or more additional PLA2 inhibitors, is co-administered with at least one metalloproteinase inhibitor (e.g. prinomastat, marimastat or batimastat, preferably prinomastat).

Notably, in some aspects, these methods of treatment obviate the need for anti-venom in treating envenomated subjects, at least in the initial stages (e.g. from immediately after the bite until up to about 24 hours or more after bite) to allow the envenomated subject to travel to a hospital or other patient care facility for further diagnosis and/or treatment with an anti-venom agent or anti-venom (e.g. specific antibody) or small molecule combination (often varespladib/methyl varespladib). The anti-venom agents and the anti-venom small molecule(s) combination may be administered in combination with MMP inhibitors such as doxycycline, cefixime or prinomastat. Quite unexpectedly varespladib and/or methylvarespladib alone are quite effective in inhibiting the effects of envenomation by insects. Their affects in inhibiting the envenomation by snakes has been discussed in PCT publication WO2016081826A2. In other embodiments, the inclusion of AZD2716 and/or LY43371, optionally in combination with varespladib and/or methylvarespladib and optionally another PLA2 inhibitor (e.g. indoxam or methylindoxam among other direct or indirect inhibitors—eg gabexate), and one or more of prinomastat, chemostat, batimastat and marimastat and an acetylcholinesterase inhibitor (e.g. neostigmine and/or atropine) will provide a composition which is particularly useful in treating envenomated subjects in areas where venomous animals produce effects through impact on bleeding/coagulation and paralysis.

In another embodiment, the method of treatment includes at one active component (for example, at least AZD2716 and/or LY43371), in some instances at least two active components and in other instances no more than two active components selected from the group consisting of a selective sPLA2 inhibitor, a metalloproteinase inhibitor, a serine protease inhibitor, one or more acetylcholinesterase inhibitors or a nAChR agonist paired with a mAChR antagonist, a NMDA receptor antagonist and a spreading factor inhibitor to treat a subject who suffers from an envenomation, preferably at the time of envenomation and often within a period of less than about an hour after an envenomation, more no more than about 1 to about 20 minutes, more often about 1 to about 10 minutes, after an envenomation by, for example, a hymenoptera or swarming hymenoptera.

In another embodiment, the method of treatment may include effective amounts of one or more additional agents, including one or more additional PLA2, MP or SP inhibitors (as otherwise described herein, often camostate or gabexate, when used), one or more acetylcholinesterase inhibitors (for example, preferably neostigmine and/or atropine), one or more metalloproteinase inhibitors (e.g. marimastat, nafamostat or prinomastat), one or more serine protease inhibitors (e.g. nafamostat), at least one spreading factor inhibitor and at least one NMDA receptor antagonist, among others, including lidocaine and/or bupivacaine which may be included in effective amounts in order to increase blood flow in the area while providing pain relief in which the composition is administered in order to increase biodistribution to the active site of the agent(s). In certain embodiments, a small molecule inhibitor such as AZD2716 and/or LY43371, optionally in combination with Varespladib and/or Methyvarespladib is combined with anti-venom to produce an unexpectedly potent treatment for envenomation.

In another embodiment, the method of treatment may include at least one active component (at least AZD2716 and/or LY43371), in some instances at least two active components and in other instances no more than two active components selected from the group consisting of a selective sPLA2 inhibitor (which also may function as an effective metalloproteinase inhibitor), a metalloproteinase inhibitor, a serine protease inhibitor, one or more acetylcholinesterase inhibitors, a NMDA receptor ant, an L-aminooxidase inhibitor, a hyaluronidase inhibitor and a spreading factor inhibitor to treat a subject who suffers from an envenomation, preferably at the time of envenomation and often within a period of several hours to less than about an hour after an envenomation, more often no more than about 1 to about 20 minutes, more often about 1 to about 10 minutes, after a bite or sting by, for example, a wasp or bee.

In one embodiment, in addition to AZD2716 and/or LY43371, at least one agent selected from the group consisting of a 1H-Indole-3-glyoxylamide compound, especially varespladib and/or methylvarespladib, and optionally an SP inhibitor such as camostat (N,N-dimethylcarbamoylmethyl,4-4-guanidinobenzoyloxy-phenylacetate or camostate) and/or gabexate (ethyl-p[6-guanidinohexanoyloxy]-benzoate methansulfonate), preferably at least varespladib, is co-administered with an acetylcholinesterase inhibitor (AChl) (e.g. neostigmine, edrophonium, or pyridostigmine, each preferably with atropine or glycopyrrolate) is used to provide a particularly effective universal antiparalytic whose significant anti-hemotoxic activity is conferred by the additional agents varespladib and/or methylvarespladib, camostat and/or gabexate. In certain embodiments, the composition to be administered contains an effective amount of at least AZD2716 and/or LY43371, and optionally versapladib or methyl varespladib which is metabolized into varespladib as its prodrug in mammals.

In another embodiment, at least AZD2716 and/or LY43371, and optionally at least varespladib and/or methylvarespladib, optionally in combination with one or more additional PLA2 inhibitors, but preferably at least varespladib, is co-administered with at least one metalloproteinase inhibitor (e.g. prinomastat, marimastat or batimastat, preferably prinomastat) and/or at least one acetylcholinesterase inhibitor (AChEI) (e.g. neostgmine and/or atropine). In certain additional embodiments, both one or more metalloproteinase inhibitors and one or more acetylcholinesterase inhibitors is included with the varespladib and/or methylvarespladib to reduce the likelihood that an envenomated subject will die or be permanently debilitated from bleeding, clotting or paralysis induced by the envenomation.

In one embodiment, the present invention relates to a method for the use of at least one PLA2 inhibitor, such as 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, optionally in combination with at least one statin, for the treatment of envenomation (e.g., snake venom, or a venomous hymenoptera bite or sting such as from bees, wasps, scorpion, spider, cnidarian or other swarming hymenoptera, as otherwise defined herein).

In one embodiment, the present invention relates to a method for the use of at least one PLA2 inhibitor, such as 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, optionally in combination with at least one statin, for the treatment of cerebral malaria.

In one embodiment, the present invention relates to a method for the use of at least one PLA2 inhibitor, such as 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, optionally in combination with at least one statin, for the treatment of hemolysis.

In one embodiment, the present invention relates to a method for the use of at least one PLA2 inhibitor, such as 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, optionally in combination with at least one statin, for the treatment of head trauma or traumatic brain injury.

In one embodiment, the present invention relates to a method for the use of at least one PLA2 inhibitor, such as 3-(5'-Benzyl-2'-carbamoylbiphenyl-3-yl) propanoic acid (Compound 4), [1,1'-Biphenyl]-3-propanoic acid, 2'-(aminocarbonyl)-α-methyl-5'-(phenylmethyl)-,(αR)—(R)-7 (also known as AZD2716 or CAS 1845753-81-2) or its biologically active analogs, optionally in combination with at least one statin, for the treatment of mast cell disease.

EXAMPLES

Example 1: In Vitro Experiments, PLA2 Inhibitors

Experiments were performed to assess sPLA2 activity using the 1,2-dithio analog of diheptanoyl phosphatidylcholine. The Bee Venom PLA2 Control was a 100 μg/mL solution of bee venom PLA2 was supplied as a positive control from kits (Abcam kit catalog number ab133089). Assay optimization, screening and dose response measurements were performed at the Yale Center for Molecular Discovery. Experiments were performed in an assay buffer containing 25 mM Tris-HCl, pH 7.5 (Cayman Chemical, Ann Arbor, MI, USA), 10 mM CaCl2 (J. T. Baker), 100 mM KCl (Sigma, St. Louis, MO, USA), 0.3% Triton X-100 (Fluka) and 454 μM DTNB (Cayman Chemical) and plated into clear, Non-Treated 384-well plates (Corning, Corning, NY, USA). Venoms (Miami Serpentarium, Punta Gorda, FL, USA, and Sigma) were reconstituted in 1× phosphate-buffered saline (Lonza, Basel, Switzerland) to a concentration of 10,000 μg/mL. Crude, unfractionated lyophilized venom purchased from Sigma (*E. carinatus* and *D. russelli*) or the Miami Serpentarium (all others) was used in all cases. Varespladib and methyl-varespladib were purchased from Chemietek (Indianapolis, IN, USA) and dissolved in DMSO for in vitro experiments and bicarbonate/dextrose for in vivo experiments. The activity of venoms with 0.375 mM 1,2-bis(heptanoyl) Glycerophosphocholine (Cayman Chemical), the sPLA2 substrate, was selected based on kinetic enzymatic assays conducted at room temperature. Concentrations of venom was selected for screening and potency studies in which high sPLA2 activity was observed relative to any background activity of no venom control wells, and for which there was negligible substrate depletion at 60 min. Instrumentation used included Tecan Aquarius (Mannedorf, Switzerland), Matrix PlateMatePlus (Hudson, NH, USA), Titertek (Pforzheim, Germany) and Thermo (Hudson, NH, USA) Multidrop liquid dispensers and Tecan infinite M1000 (Mannedorf, Switzerland) plate readers. For inhibitor and dose-response testing, 10 μL of snake venom or bee venom (+control) was added to assay plates using a multichannel pipetman (Matrix, Hudson, NH, USA) or a multidrop dispenser (Thermo, Hudson, NH, USA or Titertek, Pforzheim, Germany). Final DMSO concentrations in the assay are 0.1%. Substrate was then added in 10 μL for a final assay volume of 20 μL. Controls populations were included on each plate in replicate wells. The negative control wells were vehicle (DMSO-only) with no small molecule compound. The positive control to simulate full venom activity inhibition were wells in which no venom was added, and assay buffer added in its place. Assay signals were measured at initiation and after 60 and 120 min of reaction time at room temperature. Signals were quantified on the Tecan infiniTe M1000 plate reader measuring absorbance at 405 nm. Signals at initiation were subtracted from the signals at 60 min or 120 min. These background-corrected values were normalized to the mean of replicate negative and positive control wells within the plate. To define the normalization scale, the mean of the negative control well signals, representing full venom activity, was normalized to 100% effect and the mean of positive control well signals, representing complete inhibition of venom activity, was normalized to 0% effect. And wells within the plate were scaled accordingly. These calculations were performed in MicroSoft Excel. Data were transferred to GraphPad Prism (6th edition, 2014, La Jolla, CA, USA) plotted and fit to models, such that $IC_{50}$ or $EC_{50}$ values could be determined. Tests of significance were calculated by Student's t and all others were descriptive.

TABLE 1 demonstrates that varespladib, methyl-varespladib, LY433771 and 3-(5'-Benzyl-2'-carbamoylbiphenyl-3-yl)propanoic acid ("Compound 4" in Table 1) have very weak inhibitory activity in vitro against bee venom sPLA2, as compared to viper venoms from North America, India/Asia and Europe. $IC_{50}$ (μM) were calculated using chromogenic assays for sPLA2 inhibition after 60 of incubation. While demonstrating high degrees of potency against snake venoms, no inhibitor tested had clinically meaningful potency against bee venom sPLA2.

TABLE 1

| | $IC_{50}$, μM for each venom inhibitor | | | | |
|---|---|---|---|---|---|
| Venom | CroFab ® | Varespladib | Me-Varespladib | LY433771 | Compound 4 |
| *A. contortrix* | 0.13 | 0.0009 | 0.43 | 0.002 | 0.088 |
| *C. atrox* | 0.04 | 0.0007 | 0.2 | 0.001 | — |
| *C. adamanteus* | 0.04 | 0.0008 | 0.36 | 0.001 | — |
| *V. berus* | — | 0.0008 | 0.17 | 0.001 | 0.17 |
| *V. russelli* | — | 0.0004 | 0.08 | 0.001 | — |
| *C. terrificus* | — | 0.021 | — | — | 0.67 |
| Bee venom | — | 12-18 | — | 7.3-9.2 | >70 |

Example 2: In Vivo Experiments, PLA2 Inhibitors

CD-1 mice (Charles River Laboratories) were randomly assigned to treatment groups (n=10 each) and received IV administration in the tail vein bee venom (5 mg/kg) with and without varespladib (5 mg/kg IV which was mixed immediately prior to administration or given sequentially with venom administered first. For SQ administration, venom was administered first followed by 15 mg/kg varespladib by SQ route where SQ=Subcutaneous). Experiments were performed at a Pacific Biolabs (Hercules, CA, USA) so the investigators did not conduct the experiments and were blinded as such. Animals were monitored for signs of toxicity for approximately 36 h. Surviving animals were euthanized following the 36-h observation. Tissues were grossly examined but not collected for further processing.

TABLE 2 AND FIG. 1 demonstrate the effect of PLA2 inhibition on the survival of mice envenomated with bee venom. 10/10 mice receiving IV injections of bee venom at 5 mg/kg survived 30 hours when co-treated with ~10 mg/kg varespladib (TABLE 2, Treatment Group 1), while 7 of 10 (70%) of mice treated with bee venom (5 mg/kg) died within an average of 18 hours with only 3 (30%) surviving 30 hours to the end of the observation period (TABLE 2, Treatment Group 2). FIG. 1 demonstrates the % survival of mice of varying routes of PLA2 inhibitor treatment following administration of highly lethal doses of bee venom IV. There was an 80% survival of the 5 mice that received bee venom at 5 mg/kg intravenously when treated intravenously (IV) in a different vein (1 minute post-envenomation) with 10 mg/kg varespladib. There was a uniformly prolonged survival of the 5 mice that received bee venom at 5 mg/kg intravenously when treated subcutaneously (SQ) with 25 mg/kg varespladib immediately after envenomation compared to controls. There was just 16% (1 of 6 mice) survival of the 6 mice that received only bee venom at 5 mg/kg intravenously. The surviving mouse inadvertently received SQ rather than IV venom.

TABLE 2

| Group | Treatment | Dose Route Dose Level | Animal Number | Dose Time | Time of Death | Time to Death (min) |
|---|---|---|---|---|---|---|
| 1 | Crude bee venom | IV | 1 | 0813 | n/a | n/a |
| | (filtered) | 5 mg/kg | 2 | 0813 | n/a | n/a |
| | (Test Article 1) + | (venom) | 3 | 0814 | 0649 | 22 h, 35 min |
| | Excipient | | 4 | 0815 | 0649 | 22 h, 34 min |
| | | | 5 | 0815 | n/a | n/a |
| | | | 6 | 0816 | 0649 | 22 h, 33 min |
| | | | 7 | 0817 | 1700 | 8 h, 43 min |
| | | | 8 | 0817 | 0903 | 24 h, 46 min |
| | | | 9 | 0818 | 1154 | 3 h, 36 min |
| | | | 10 | 0819 | n/a | n/a |
| | | Average: | | | | 1048 |
| 2 | Crude bee venom | IV | 11 | 0819 | n/a | n/a |
| | (filtered) | 5 mg/kg | 12 | 0820 | n/a | n/a |
| | (Test Article 1) + | (venom) | 13 | 0821 | n/a | n/a |
| | Varespladib | 10 mg/kg | 14 | 0821 | n/a | n/a |
| | (Test Article 4) | (varespladib) | 15 | 0822 | n/a | n/a |
| | | | 16 | 0823 | n/a | n/a |
| | | | 17 | 0823 | n/a | n/a |
| | | | 18 | 0824 | n/a | n/a |
| | | | 19 | 0825 | n/a | n/a |
| | | | 20 | 0825 | n/a | n/a |
| | | Average: | | | | n/a |

The survival benefit of mice in the setting of lethal hymenoptera envenomation is highly surprising in light of the PLA2 inhibitor (in this example, varespladib) having activity only <1/5,000-1/100,000 the potency of PLA2 inhibitors in human and snake venom assays. In vitro, varespladib and methyl-varespladib are not potent inhibitors of bee venom PLA2, a Type III sPLA2 isoform typical of invertebrate venoms and human mast cells, for example. Similarly, Compound 4 has virtually no effect on bee venom at any concentration (see Table 1). It is posited that both direct and indirect effects of PLA2 inhibition are responsible for this survival effect, thus reducing the likelihood of catastrophic coagulopathies, tissue damage and kidney failure, among other venom-, intracellular parasitic infections and their sequelae (e.g. cerebral malaria)- or trauma-induced pathology eliciting neuronal damage and unusual complement mediated hemolytic anemias (e.g. paroxysmal nocturnal hemoglobinuria (PNH)).

Example 3: Prevention of Hemolysis: In Vitro Experiments PLA2 Inhibitors

Figure 2:
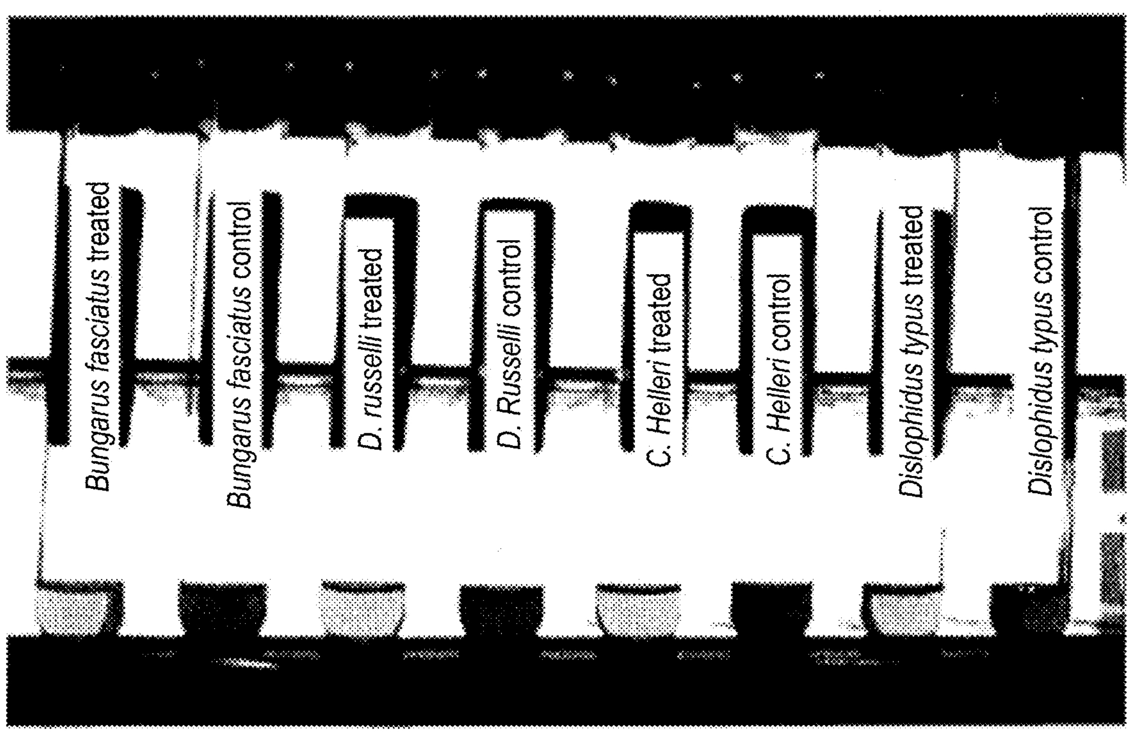
FIGS. 2-4 show that varespladib alone or in combination with mannitol solution prevents gross hemolysis in ex vivo human blood treated with a variety of viper venoms.
Figure 3:
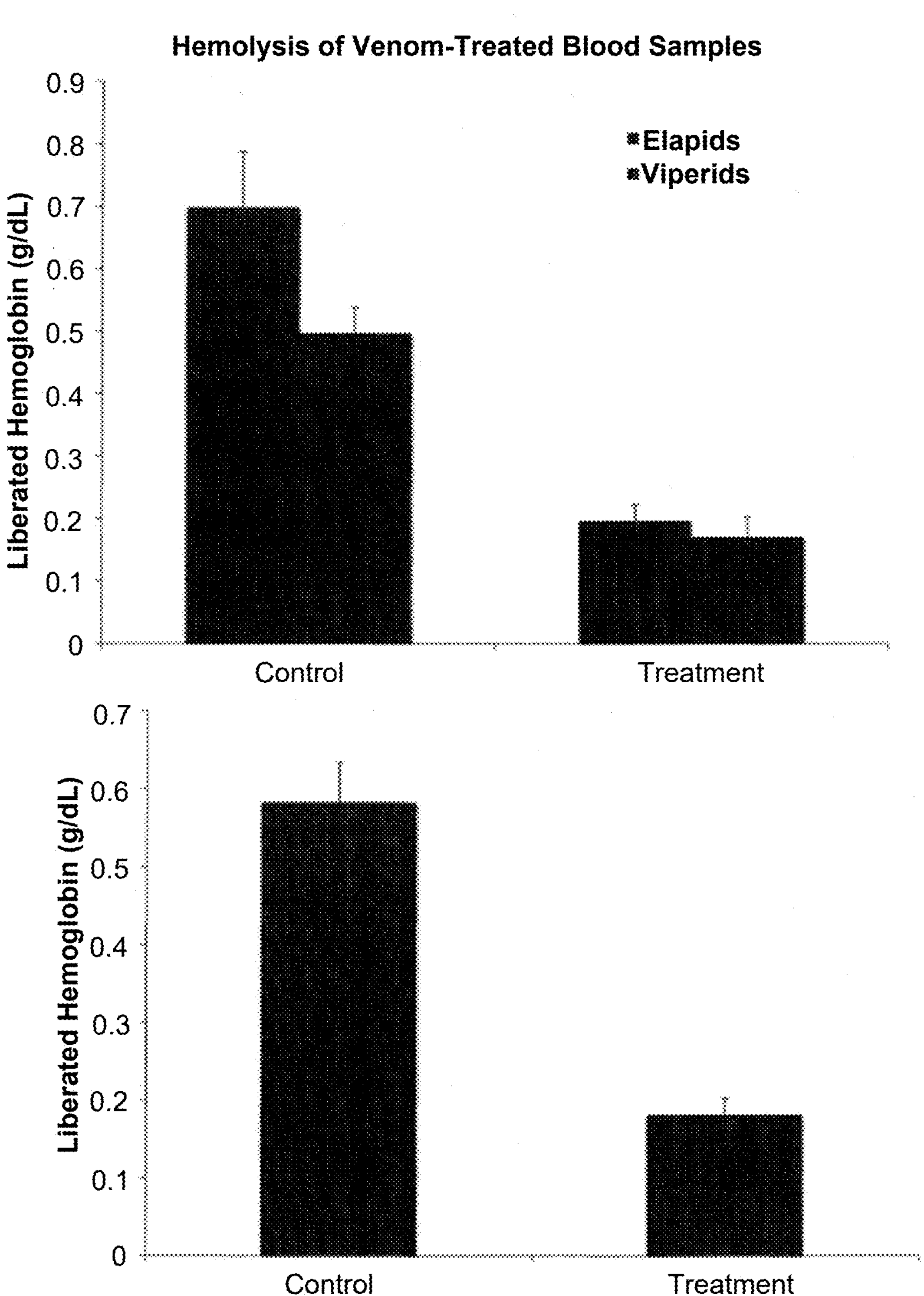
Figure 4:
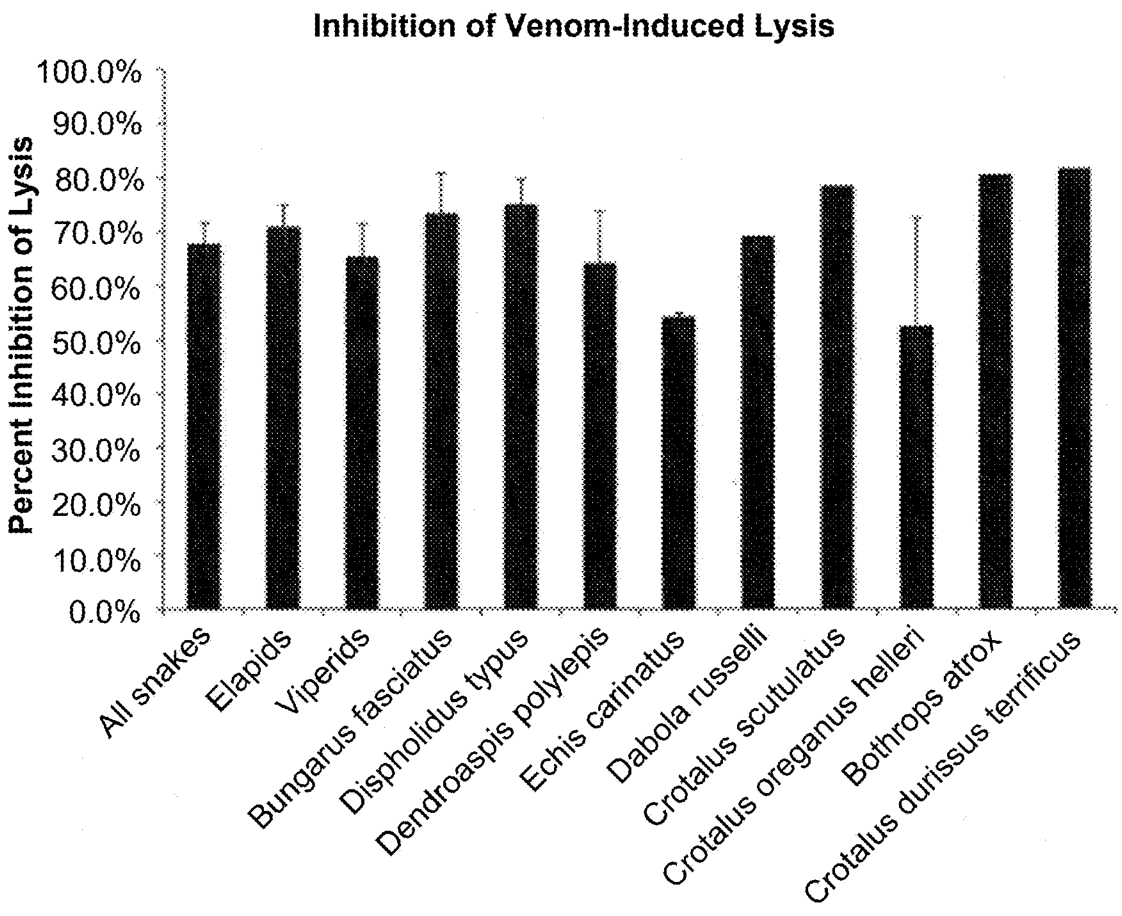

FIGS. 2-4 demonstrate that varespladib in combination with mannitol in a citrate/dextrose saline solution prevents gross hemolysis ex-vivo in whole human blood treated with a variety of unrelated snake venoms (Elapid, viperid, colubrid). In FIG. 2, gross hemolysis is visible in the supernatant containing free hemoglobin from ruptured red blood cells decanted from whole human blood following exposure to high doses of snake venom and treatment with varespladib/mannitol/bicarbonate/citrate/dextrose (treated) or excipient (mannitol/bicarbonate/citrate/dextrose) (control). In each case, there was no gross hemolysis in the treated human blood (venom and drug/excipient+/−controls). In each case, there was clear gross hemolysis in the venom/excipient only controls.

In this example, centrifuged samples containing 3 cc of venous human blood, following 60 minutes of incubation with (1) 100 μL varespladib/mannitol/citrate at a ratio of 1:2:1, dissolved 1:1 in bicarbonate 8.4% and 10% dextrose in water 1:3 with venom: (a) 100 μL Boomslang venom (*Dispholidus typus*), a Colubrid snake stock concentration 10 mg/mL, or 50 μL Banded Krait (Elapid) venom (*Bungarus fasciatus*) stock concentration 1 mg/mL; or (2) 100 μL varespladib/mannitol/citrate at a ratio of 1:2:1, dissolved 1:1 in bicarbonate 8.4% and 10% dextrose in water 1:3 with Viperid venom: (a) 100 μL of Russell's viper venom (*Daboia russelli*) stock concentration 6 mg/mL or stock solution 10 mg/mL, or (b) 100 μL Western Pacific Rattlesnake venom (*Crotalus helleri*) stock concentration 10 mg/mL. Control samples contained excipients alone or varespladib+excipient. Hematocrit values for each sample were assessed, to estimate the amount of liberated hemoglobin (g/dL) after lysis with distilled water. FIG. 3 (upper) shows the corresponding hematocrit values of liberated hemoglobin (g/dL) for the control and treatment samples, averaging all control elapid samples (n=3), all control viperid samples (n=3), all elapid treatment samples (n=3) an all Viperid treatment samples (n=3). FIG. 3 (lower) further demonstrates the benefit of applying the venom/host PLA2 inhibiting effects of varespladib with mannitol, showing an average of all control samples (n=3) and all venom-treatment samples (n=3). FIG. 4 demonstrates the normalized percent inhibition of venom-induced lysis by snake family (Elapids, Colubrid & Viperids) and by snake species.

Example 4: In Vitro Experiments, PLA2 Inhibitors+Statins

Figure 5A:
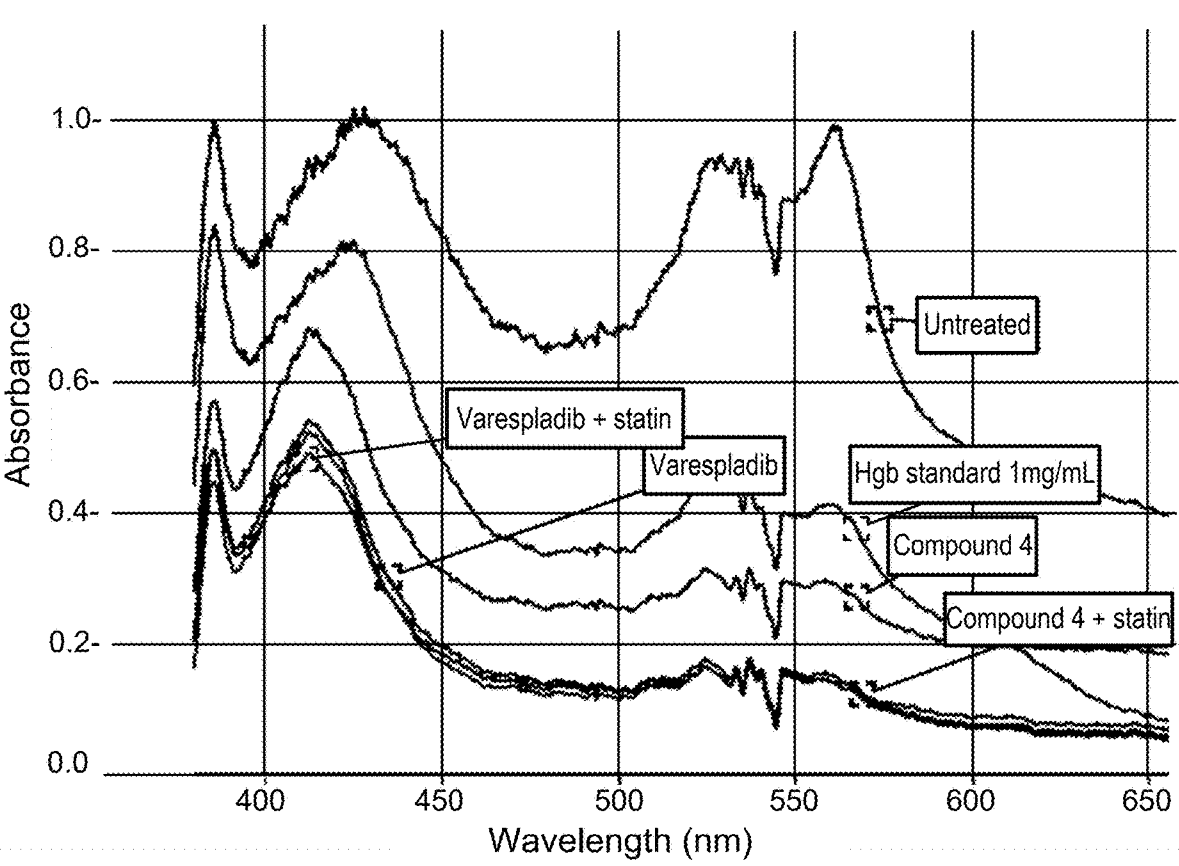
FIGS. 5A-5B show that statins, alone and in combination with PLA2 inhibitors, reduce hemolysis ex vivo in human blood treated with different snake venoms.
Figure 5B:
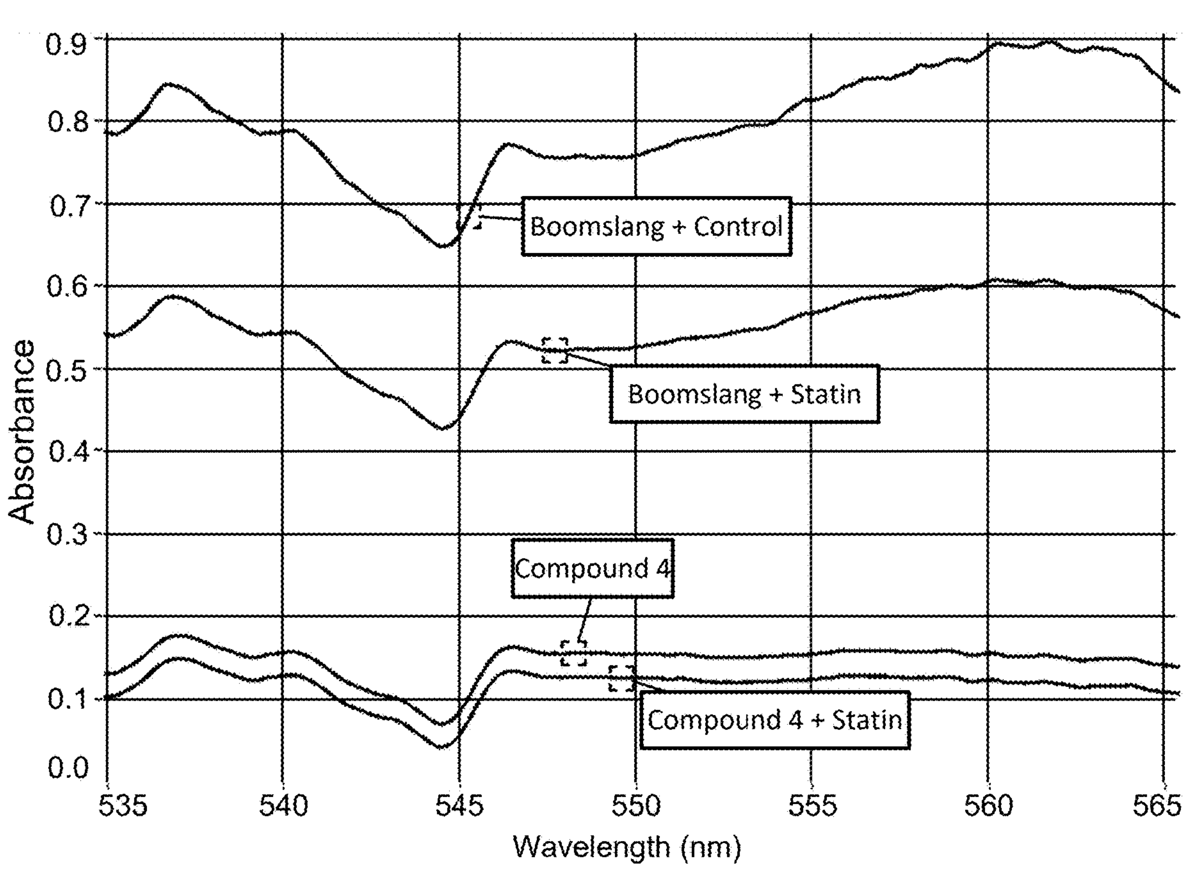

FIG. 5A-B shows that statins enhance the effect of an sPLA2 inhibitor on preventing the hemolysis of ex vivo whole human blood treated with elapid venom. In FIG. 5A, 4 cc of venous human blood was incubated with 50 μL *M. Fulvius* venom stock concentration 5 mg/mL and an sPLA2 inhibitor (varespladib at 1 uM, or 3-(5'-Benzyl-2'-carbamoylbiphenyl-3-yl)propanoic acid, herein referred to as Compound 4, at 1 uM) with or without soluble simvastatin "InSol®" (1 uM) for 90 minutes. Control samples contained venom without drug treatment or venom plus simvastatin. Hemoglobin (Hgb) absorption spectra represented in FIG. 5A provide the absorbance vs. wavelength values, indicating the degree of hemolysis. FIG. 5A demonstrates the enhanced anti-hemolytic activity of Compound 4 plus a statin. Inhibition of hemolysis by Varespladib remained unchanged with the addition of statin in the venoms tested, suggesting the addition of a statin to an sPLA2-inhibitor could be advantageous.

In FIG. 5B, 3 cc of venous human blood was incubated with 100 μL Boomslang (*Dispholidus typus*) venom stock concentration 10 mg/mL and Compound 4 (1 uM) with or without soluble simvastatin (1 uM) for 90 minutes. Control samples contained untreated blood. FIG. 5B demonstrates the anti-hemolytic activity of Compound 4 both with and without a statin.

Example 5: In Vitro Experiments, PLA2 Inhibitors Reduce Histamine and Protect from Osmotic Fragility TABLE 3 shows that both varespladib and Compound 4 reduce histamine production or release in human blood. In this example, 3 cc human blood from a donor prone to LRR was collected and shipped to Quest on ice pursuant to Quest collection protocol 36586 and incubated with (a) Mannitol+ Compound 4 (10 uM), (b) Varespladib (10 uM), or (c) Mannitol alone (excipient). Samples were processed for plasma histamine levels, compared with the Mannitol-only control.

TABLE 3

| Sample | Plasma Histamine ng/ml |
|---|---|
| Mannitol excipient (control) | 15.9 |
| Compound 4 | 10.1 |
| Varespladib | 5.1 |

Figure 6:
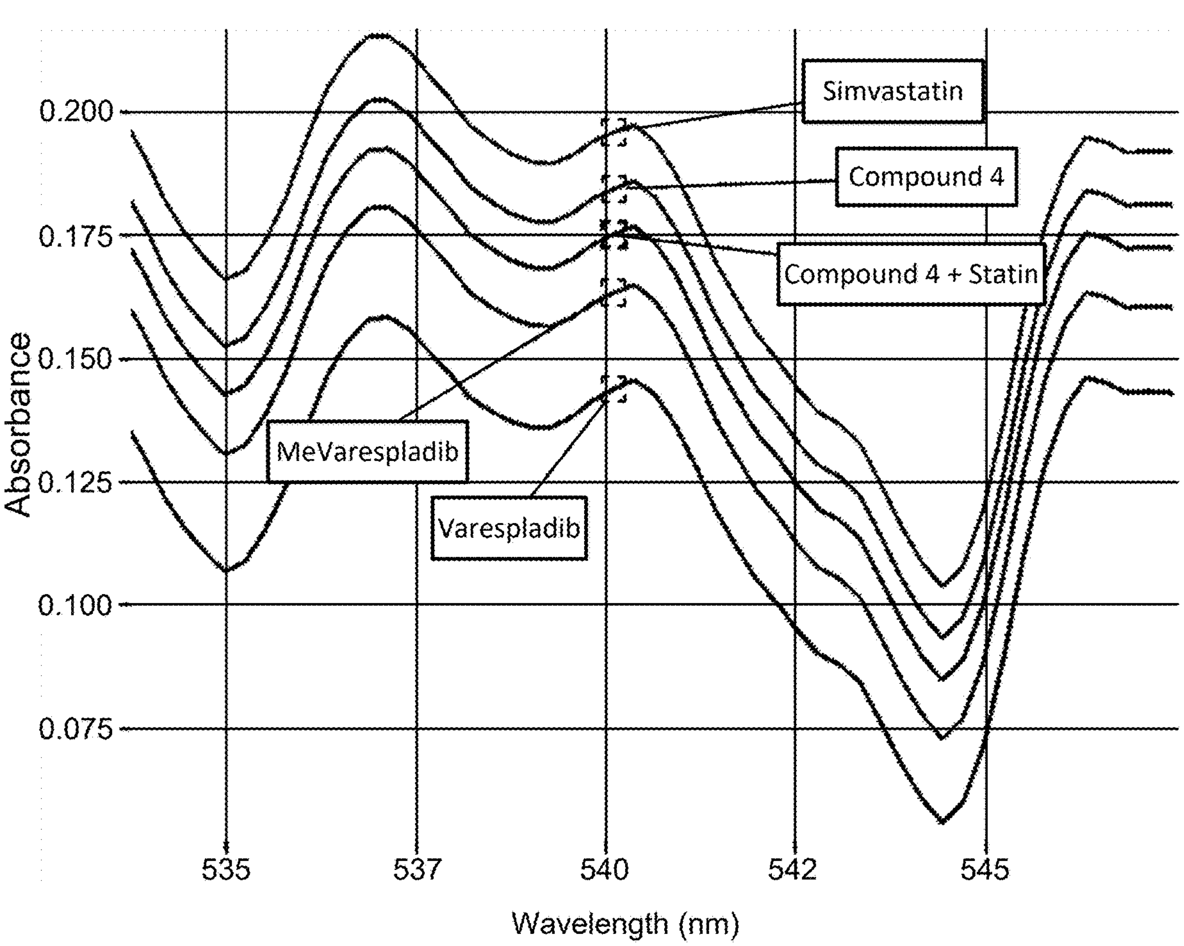
FIG. 6 shows that PLA2 inhibitors reduce osmotic fragility in human red blood cells.

FIG. 6 shows that PLA2 inhibitors protect human red blood cells from osmotic fragility in a solution of half normal saline (0.45%). In this example, 100 μL venous human blood was incubated in half normal saline with (a) soluble simvastatin (1 μM), (b) Varespladib (1 μM), (c) Me-Varespladib (1 μM), (d) Compound 4 (1 μM), (e) Compound 4+Simvastatin or (f) Mannitol excipient alone (control) for (120 minutes followed by centrifugation per the protocol described by de Freitas et al *J. Memb. Biol.* 2010). Hemoglobin (Hgb) absorption spectra represented in provide the absorbance vs. wavelength values, indicating relative degree of hemolysis. FIG. 6 demonstrates that the combination of simvastatin and compound 4 improved the performance of compound 4 protecting red blood cells from hemolysis. Compound 4 is thought to inhibit uptake of statins, but has been shown to have virtually identical sPLA2 potency compared to varespladib. See Giordanetto, F., et al., *ACS Med. Chem. Lett.* 2016:7, 884-889. It was surprising that Compound 4 is not as potent against snake venom sPLA2s and that the addition of statin improved Compound 4's ability to prevent red-cell ruptures in conditions promoting osmotic fragility.

TABLE 4

| Drug Name 10 μM | *C. atrox* venom MP inhibition % effect | *E. carinatus* venom MP inhibition % effect | *M. fulvius* venom sPLA2 inhibition % effect |
|---|---|---|---|
| Simvastatin | 4.03 | −0.20 to 4.61 | 16.41 |
| Itavastatin | 5.09 | 0.48 | — |
| Pravastatin | 2.27 | 4.02 | 6.90 |
| Mevastatin | 7.17 | −1.89 to 3.82 | 16.29 |
| Lovastatin | — | −1.89 | 11.09 |

TABLE 4 shows that statins had no or minimal effect on MPs and minimal but surprisingly present effect on the screened sPLA2 venom, *M. fulvius* venom. As shown in FIGS. 5 & 6, the addition of Simvastatin to Compound 4 (which is known to inhibit statin uptake via 1B1) improves the performance of Compound 4 compared to Compound 4 without Simvastatin and in comparison to Varespladib to reduce hemolysis in whole blood exposed to high concentrations of *M. fulvius* (eastern coral snake) and *D. typus* (Boomslang) venoms. Statins had no or minimal effect on MPs and a previously unknown effect on sPLA2 from the venom of *M. fulvius* venom at just 10 PM. *M. fulvius* (Eastern coral snake, an elapid) sPLA2 inhibition by different HMG-CoA reductase inhibitors ("statins"): Simvistatin 16.41%, Pravastatin 6.9%, Mevastatin 16.29%, Lovastatin 11.09%. Snake venom metalloprotease inhibition for *C. atrox* and *E. carinatus* (Western diamondback rattlesnake and Saw-scale vipers): Simvastatin, −0.20 to 4.61%; Itavastatin 0.48 to 5.09%; Pravastatin 2.27 to 4.02%; Mevastatin −1.89 to 7.17%; Lovastatin −1.89% for *E. carinatus.*

Figure 7:
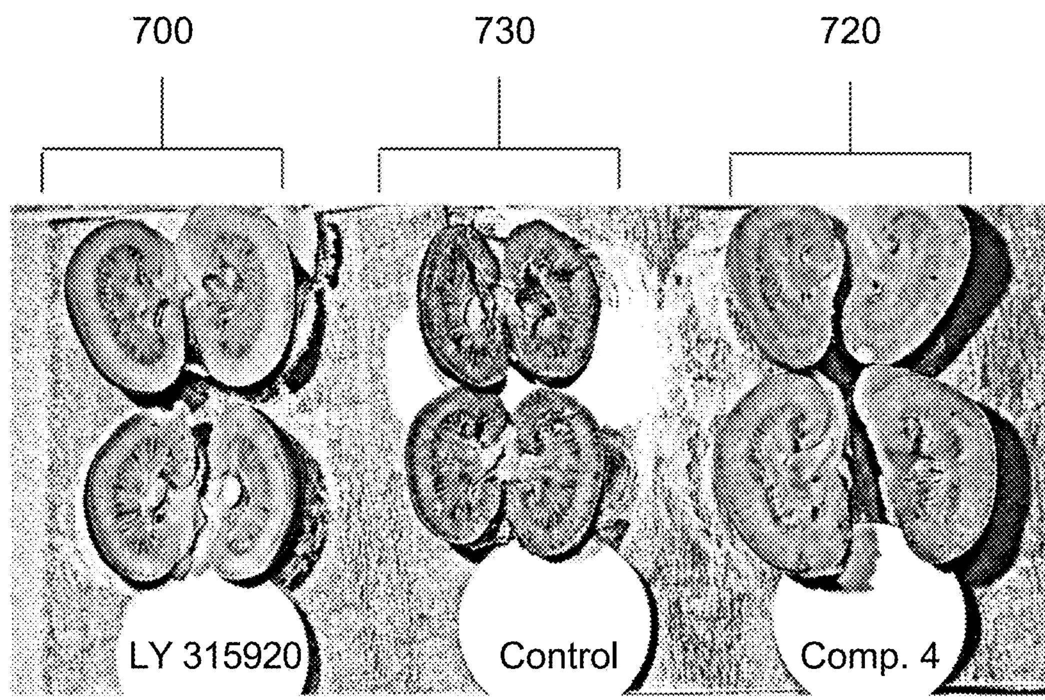
FIGS. 7-8 show that PLA2 inhibitors prevent venom-induced acute kidney injury (AKI) even in venoms with very little sPLA2 activity or very high Type 11 sPLA2 activity.

FIG. 7 shows that varespladib and Compound 4 each protect mouse kidneys from pigment nephropathy, hydronephrosis and other gross structural damage in the setting of sublethal envenomation with boomslang venom (which has a very low sPLA2 content compared to MP content) or bee venom (Type 11 sPLA2). Per the protocol detailed above in Example 1, a single dose of Varespladib (LY315920) or 3-(5'-Benzyl-2'-carbamoylbiphenyl-3-yl) propanoic acid (Comp. 4) was administered at same time as the venom. Sham treated mice were used as a control. Kidneys from Varespladib-treated animals 700 demonstrate minimal signs of acute kidney injury. Kidneys from Comp. 4-treated animals 720 demonstrate comparably minimal signs of acute kidney injury compared to Varespladib despite inferior potency (IC50s) against snake venom, in vitro. Kidneys from control-treated animals 730 demonstrate severe signs of acute injury including pigment nephropathy, hemorrhage and tissue degradation. These results demonstrate that even 24 hours after venom/venom-drug administration, PLA2 inhibitors protect the kidneys from venom-induced nephropathy even when direct inhibition of venom sPLA2 is sub-optimal.

Figure 8:
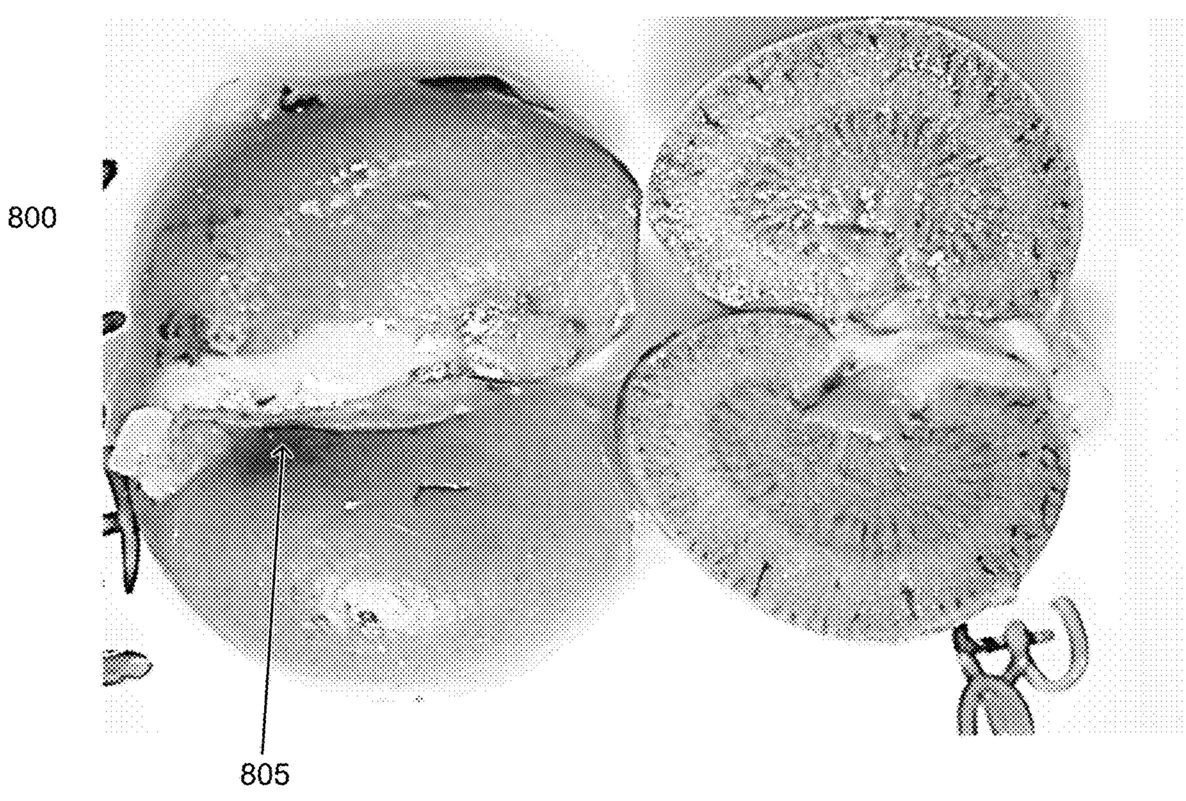
Figure 8:
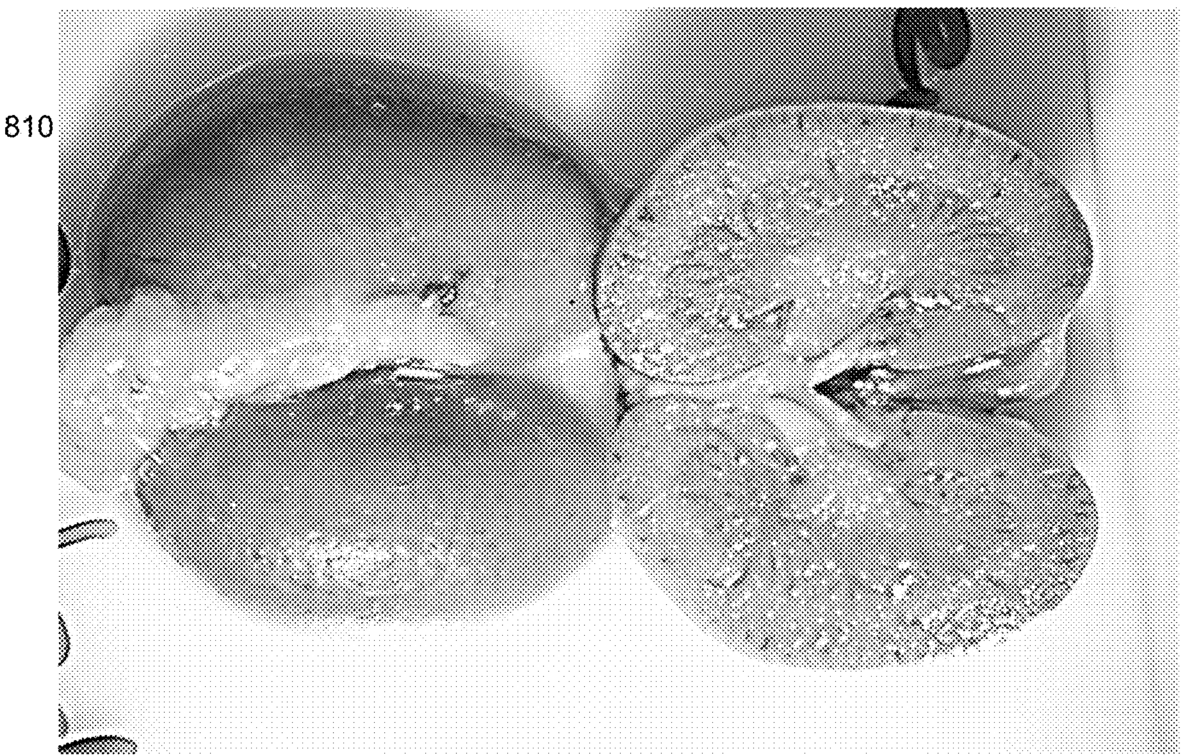

FIG. 8 shows decreased levels of pigment nephropathy 805 and hyperemia in mouse kidneys following sublethal envenomation with whole bee (*Apis mellifera*) venom without treatment 800 or with initial dose of Varespladib (LY315920) 810 followed by oral methylvarespladib (LY333013) taken ad libitum in diet). Per the protocol detailed above in Example 1, a single dose of Varespladib (LY315920) was administered at the same time as the bee venom. This was followed by ad libitum feeding of methylvarespladib (LY333013) to LY315920 treated mice and diet containing excipient only to control mice. Kidneys were examined 36 hours after envenomation and demonstrated excellent protection from AKI. The protocol also exemplifies how IV and PO dosing regimens can be interchanged.

The invention claimed is:

1. A method of treating a subject for envenomation by a vertebrate or invertebrate animal, comprising administering to the subject a small molecule inhibitor of secretory phospholipase A2 (sPLA2) selected from compounds having the structure shown in Formula I and pharmaceutically acceptable salts thereof:

Formula I

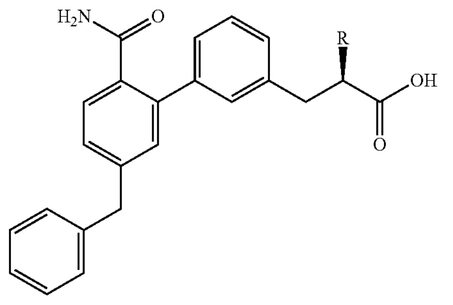

wherein R is H (Compound 4) or —$CH_3$ (AZD 2716).

2. The method according to claim 1, wherein the animal is a snake.

3. The method according to claim 1, wherein the sPLA2 inhibitor is adapted to be administrable orally or by injection within 6 hours of the envenomation.

4. The method according to claim 1, wherein the sPLA2 inhibitor is administered to the subject simultaneously or sequentially with an anti-venom antibody or fragment thereof.

5. The method according to claim 1, wherein the sPLA2 inhibitor is administered to the subject simultaneously or sequentially with a metalloproteinase inhibitor.

6. The method according to claim 5, wherein the metalloproteinase inhibitor is selected from prinomastat, marimastat, vorinostat, batimastat, and pharmaceutically acceptable salts thereof.

7. A method of treating a subject for envenomation by a vertebrate or invertebrate animal, comprising simultaneously or sequentially administering to the subject a combination of compounds comprising a small molecule inhibitor of secretory phospholipase A2 (sPLA2) and a statin.

8. The method according to claim 7, wherein the small molecule inhibitor of sPLA2 is selected from varespladib, methylvarespladib, indoxam, methyl indoxam, {9-[(phenyl) methyl]-5-carbamoylcarbazol-4-yl} oxyacetic acid (LY433771), 2'-(aminocarbonyl)-α-methyl-5'-(phenylmethyl)-,(αR)—(R)-7 (AZD2716), 3-(5'-benzyl-2'-carbamoylbiphenyl-3-yl) propanoic acid (Compound 4), and pharmaceutically acceptable salts thereof.

9. The method according to claim 7, wherein the statin is selected from atorvastatin, cerivastatin, fluvastatin, lovastatin, a monacolin, mevastatin, pitavastatin, pravastatin, rosuvastatin, simvastatin, and pharmaceutically acceptable salts thereof.

10. The method according to claim 7, wherein the animal is a snake.

11. The method according to claim 1, which is effective in preventing acute kidney injury caused by the envenomation.

12. The method according to claim 1, which is effective in protecting against effects of a lethal dose of venom or a mast cell proliferation or degranulation disorder.

13. The method according to claim 1, which is effective in preventing hemolysis caused by the envenomation.

14. The method according to claim 1, which is effective in preventing cerebral edema caused by the envenomation.

15. The method according to claim 7, which is effective in preventing acute kidney injury caused by the envenomation.

16. The method according to claim 7, which is effective in protecting against effects of a lethal dose of venom or a mast cell proliferation or degranulation disorder.

17. The method according to claim 7, which is effective in preventing hemolysis caused by the envenomation.

18. The method according to claim 7, which is effective in preventing cerebral edema caused by the envenomation.

19. The method according to claim 1, wherein the sPLA2 inhibitor is contained in an injection device that is configured to deliver an effective dose of the sPLA2 inhibitor into a subject as field treatment upon realization that the subject has been envenomed.

20. The method according to claim 7, wherein the compounds are contained in an injection device that is configured to deliver an effective dose of said combination of compounds into a subject as field treatment upon realization that the subject has been envenomed.

* * * * *